(12) United States Patent
Newman et al.

(10) Patent No.: US 11,266,129 B2
(45) Date of Patent: Mar. 8, 2022

(54) MURINE MODEL OF FETAL/NEONATAL ALLOIMMUNE THROMBOCYTOPENIA

(71) Applicant: VERSITI BLOOD RESEARCH INSTITUTE FOUNDATION, INC., Milwaukee, WI (US)

(72) Inventors: Peter J. Newman, Bayside, WI (US); Huiying Zhi, Brookfield, WI (US)

(*) Notice: Subject to any disclaimer, the term of this patent is extended or adjusted under 35 U.S.C. 154(b) by 0 days.

(21) Appl. No.: 16/674,804

(22) Filed: Nov. 5, 2019

(65) Prior Publication Data

US 2021/0127648 A1 May 6, 2021

(51) Int. Cl.
| | |
|---|---|
| *G01N 33/566* | (2006.01) |
| *A01K 67/027* | (2006.01) |
| *C07K 14/705* | (2006.01) |
| *G01N 33/50* | (2006.01) |
| *C12N 15/89* | (2006.01) |
| *G01N 33/577* | (2006.01) |

(52) U.S. Cl.
CPC .... *A01K 67/0275* (2013.01); *C07K 14/70546* (2013.01); *C12N 15/89* (2013.01); *G01N 33/5047* (2013.01); *G01N 33/577* (2013.01); *A01K 2217/07* (2013.01); *A01K 2227/105* (2013.01); *A01K 2267/0387* (2013.01)

(58) Field of Classification Search
None
See application file for complete search history.

(56) References Cited

U.S. PATENT DOCUMENTS

| | | | |
|---|---|---|---|
| 4,736,866 A | 4/1988 | Leder | |
| 4,870,009 A | 9/1989 | Evans | |
| 4,873,191 A | 10/1989 | Wagner | |
| 4,873,316 A | 10/1989 | Meade | |
| 5,589,604 A | 12/1996 | Drohan | |
| 5,602,306 A | 2/1997 | Townes | |
| 5,639,457 A | 6/1997 | Brem | |
| 5,639,940 A | 6/1997 | Garner | |
| 5,880,327 A | 3/1999 | Lubon | |
| 5,959,171 A | 9/1999 | Hyttinin | |
| 6,166,288 A | 12/2000 | Diamond | |
| 6,204,431 B1 | 3/2001 | Prieto | |
| 6,218,595 B1 | 4/2001 | Giros | |
| 6,255,554 B1 | 7/2001 | Lubon | |
| 6,331,658 B1 | 12/2001 | Cooper | |
| 6,339,183 B1 | 1/2002 | Sun | |
| 6,344,596 B1 | 2/2002 | Velander | |
| 6,791,006 B2 | 9/2004 | Nezu | |
| 7,022,893 B1 | 4/2006 | Takeda | |

OTHER PUBLICATIONS

Zhu (Nature Communications, pp. 1-13, 2019) (Year: 2019).*
Tratar (Front. Oncol, 8(268): 1-18, 2018) (Year: 2018).*
Markossian (Journal of Molecular Endocrinology, 57: R81-R92, 2016) (Year: 2016).*
Yan et al. (2000, Science 290:523-527 (Year: 2000).*
Bowie et al., 1990, Science 247:1306-1310 (Year: 1990).*
Ahlen Mt, et al. T-cell responses associated with neonatal alloimmune thrombocytopenia: isolation of HPA-1a-specific, HLA-DRB3*0101-restricted CD4+T cells. Blood. 2009;113(16):3838-3844.
Barron-Casella EA, et al. Construction of a human platelet alloantigen-1a epitope(s) within murine glycoprotein IIIa: identification of residues critical to the conformation of the antibody binding site(s). Blood. 1999;93(9):2959-2967.
Beer J, et al. Evidence that platelet glycoprotein IIIa has a large disulfide-bonded loop that is susceptible to proteolytic cleavage. JBiolChem. 1989;264:17564-17573.
Bonacossa IA, et al. Alloimmune thrombocytopenia of the newborn: neurodevelopmental sequelae. Am J Perinatol. 1996; 13(4):211-215.
Bowditch RD, et al. Localization of a PIA1 epitope to the amino terminal 66 residues of platelet glycoprotein IIIa. Blood. 1992;79:559-562.
Bussel J. Diagnosis and management of the fetus and neonate with alloimmune thrombocytopenia. J Thromb Haemost. 2009;7 Suppl 1:253-257.
Davoren A, et al. Human platelet antigen-specific alloantibodies implicated in 1162 cases of neonatal alloimmune thrombocytopenia. Transfusion. 2004;44(8): 1220-1225.
Dreyfus M, et al. Frequency of immune thrombocytopenia in newborns: a prospective study. Immune Thrombocytopenia Working Group. Blood. 1997;89(12):4402-4406.
Duquesnoy Rj. Structural epitope matching for HLA-alloimmunized thrombocytopenic patients: a new strategy to provide more effective platelet transfusion support? Transfusion. 2008;48(2):221-227.
Eksteen M, et al. Characterization of a human platelet antigen-1 a-specific monoclonal antibody derived from a B cell from a woman alloimmunized in pregnancy. J Immunol. 2015;194(12):5751-5760.
Plug F, et al. A 13-mer peptide straddling the leucine33/proline33 polymorphism in glycoprotein IIIa does not define the PIA1 epitope. Blood. 1991;77:1964-1969.
Ghevaert C, et al. HPA-1a antibody potency and bioactivity do not predict severity of fetomatemal alloimmune thrombocytopenia. Transfusion. 2007;47(7):1296-1305.
Giovangrandi Y, et al. Very early intracranial haemorrhage in alloimmune fetal thrombocytopenia. Lancet. 1990;336(8710):310.
Goldberger A, et al. Effect of single amino acid substitutions on the formation of the PIA and Bak alloantigenic epitopes. Blood. 1991;78:681-687.
Griffin HM, et al. A human monoclonal antibody specific for the leucine-33 (P1A1, HPA-1a) form of platelet glycoprotein IIIa from a V gene phage display library. Blood. 1995;86(12):4430-4436.
Hod E, et al., Platelet transfusion refractoriness. Br J Haematol. Jul. 2008;142(3):348-60. Epub May 28, 2008.

(Continued)

*Primary Examiner* — Anoop K Singh
*Assistant Examiner* — Magdalene K Sgagias
(74) *Attorney, Agent, or Firm* — Quarles & Brady LLP

(57) ABSTRACT

A transgenic mouse comprising T30A, S32P, Q33L, N39D, and M470Q mutations in GPIIIa, as well as methods for making the transgenic mouse and methods for using the transgenic mouse to screen test compounds are described.

2 Claims, 15 Drawing Sheets
(14 of 15 Drawing Sheet(s) Filed in Color)
Specification includes a Sequence Listing.

(56) References Cited

OTHER PUBLICATIONS

Honda S, et al. The impact of three-dimensional structure on the expression of PIA alloantigens on human integrin beta 3. Blood. 1995;86(1):234-242.

Killie MK, et al. Maternal human platelet antigen-1a antibody level correlates with the platelet count in the newborns: a retrospective study. Transfusion. 2007;47(1):55-58.

Kjeldsen-Kragh J, et al. A screening and intervention program aimed to reduce mortality and serious morbidity associated with severe neonatal alloimmune thrombocytopenia. Blood. 2007;110(3):833-839.

Kornecki E, et al. Identification of PIAI alloantigen domain on a 66 kDa protein derived from glycoprotein IIIa of human platelets. BiochimBiophysActa. 1985;818(3):285-290.

Maslanka K, et al. Molecular identification of T cells that respond in a primary bulk culture to a peptide derived from a platelet glycoprotein implicated in neonatal alloimmune thrombocytopenia. JClinInvest. 1996;98:1802-1808.

Mueller-Eckhardt C, et al. 348 cases of suspected neonatal alloimmune thrombocytopenia. Lancet. 1989;1:363-366.

Newman PJ, et al. The human platelet alloantigens, PIA1 and PIA2, are associated with a leucine33/proline33 amino acid polymorphism in membrane glycoprotein IIIa, and are distinguishable by DNA typing. JClinInvest. 1989;83:1778-1781.

Newman PJ, et al. Studies on the nature of the human platelet alloantigen, PIA1: localization to a 17,000-dalton polypeptide. MolImmunol. 1985;22:719-729.

Pidard D, et al. Interaction of AP-2, a monoclonal antibody specific for the human platelet glycoprotein IIb-IIIa complex, with intact platelets. JBiolChem. 1983;258:12582-12586.

Santoso S, et al. Antiendothelial alphavbeta3 Antibodies Are a Major Cause of Intracranial Bleeding in Fetal/Neonatal Alloimmune Thrombocytopenia. Arterioscler Thromb Vasc Biol. 2016;36(8):1517-1524.

Spencer JA, et al. Feto-matemal alloimmune thrombocytopenia: a literature review and statistical analysis. Aust N Z J Obstet Gynaecol. 2001;41(1):45-55.

Stafford P, et al. Immunologic and structural analysis of eight novel domain-deletion beta3 integrin peptides designed for detection of HPA-1 antibodies. J Thromb Haemost. 2008;6(2):366-375.

Thinn Amm, et al. Autonomous conformational regulation of beta3 integrin and the conformation-dependent property of HPA-1a alloantibodies. Proc Natl Acad Sci USA. 2018.

Turner ML, et al. Prospective epidemiologic study of the outcome and cost-effectiveness of antenatal screening to detect neonatal alloimmune thrombocytopenia due to anti-HPA-1a. Transfusion. 2005;45(12): 1945-1956.

Valentin N, et al. HLA-DRw52a is involved in alloimmunization against PIA1 antigen. HumImmunol. 1990;27:73-79.

Valentin N, et al. Involvement of the cysteine-rich domain of glycoprotein IIIa in the expression of the human platelet alloantigen, PIA1: evidence for heterogeneity in the humoral response. Blood. 1995;85(11):3028-3033.

Wang et al. "One-step generation of mice carrying mutations in multiple genes by CRISPR/Cas-mediated genome editing," Cell, 2013, 153(4):910-918.

Watkins Na, et al. HPA-1a phenotype-genotype discrepancy reveals a naturally occurring Arg93Gln substitution in the platelet beta 3 integrin that disrupts the HPA-1a epitope. Blood. 2002;99(5):1833-1839.

Weiss EJ, et al. A monoclonal antibody (SZ21) specific for platelet GPIIIa distinguishes P1A1 from P1A2. Tissue Antigens. 1995;46(5):374-381.

Williamson LM, et al. The natural history of fetomatemal alloimmunization to the platelet-specific antigen HPA-1a (PIA1, Zwa) as determined by antenatal screening. Blood. 1998;92(7):2280-2287.

Zhu G, et al. The integrin PSI domain has an endogenous thiol isomerase function and is a novel target for antiplatelet therapy. Blood. 2017;129(13):1840-1854.

PCT/US2019/059869 International Search Report and Written Opinion, dated Jun. 19, 2020.

Zhi, et al. "High-resolution mapping of the polyclonal immune response to the human platelet alloantigen HPA-1a )PI A1)," Blood Advances. 2018.

Zdravic, et al. "Fetal and neonatal alloimmune thrombocytopenia," Seminars in Fetal and Neonatal Medicine. 2016.

Semple. "Animal models of immune thrombocytopenia (ITP)," Basic Science. 2010.

* cited by examiner

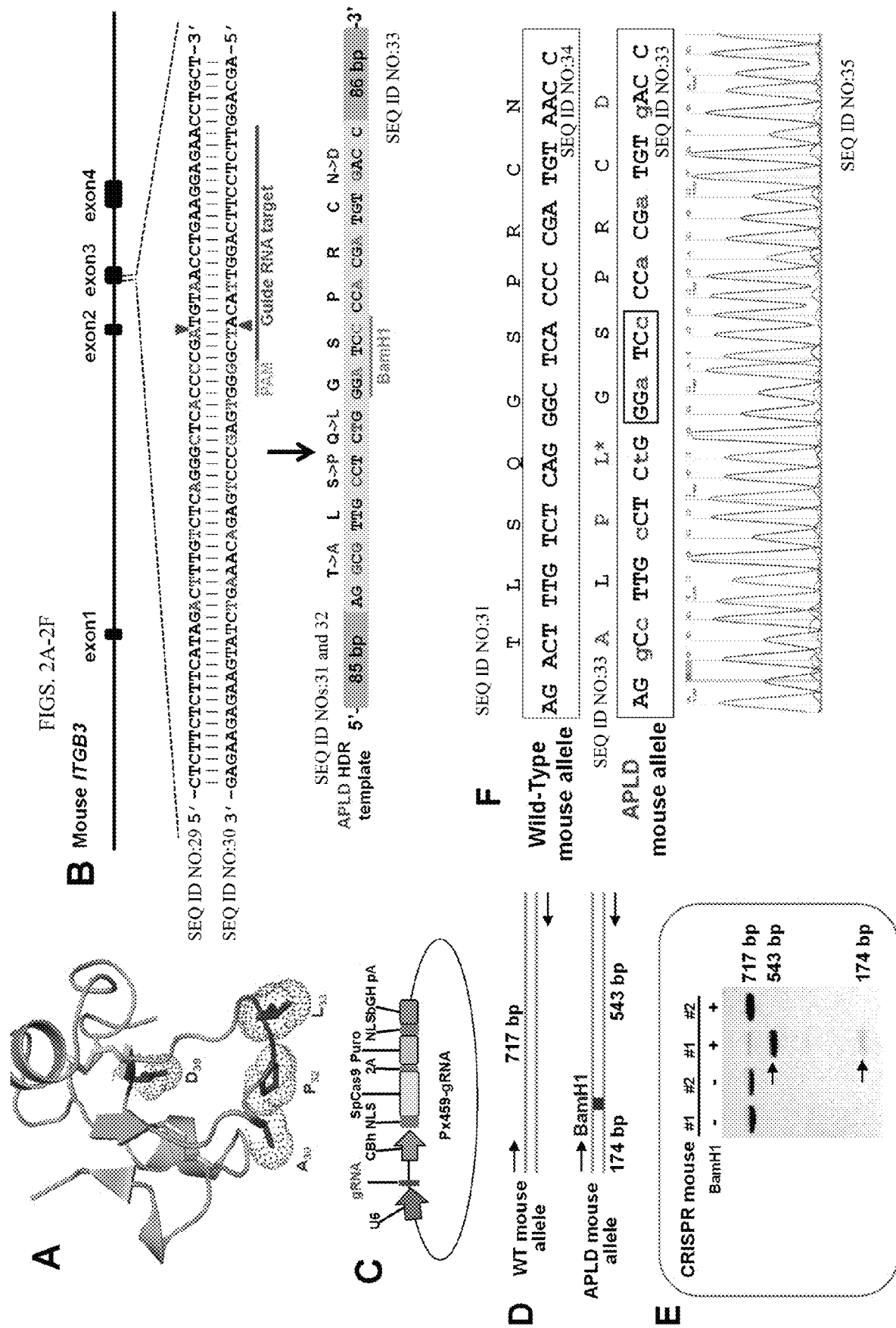

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
ttctccttca ggttacatcg                                                        20

<210> SEQ ID NO 2
<211> LENGTH: 25
<212> TYPE: DNA
<213> ORGANISM: Artificial Sequence
<220> FEATURE:
<223> OTHER INFORMATION: synthetic

<400> SEQUENCE: 2
caccgttctc cttcaggtta catcg                                                  25

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
aaaccgatgt aacctgaagg agaac                                                  25

<210> SEQ ID NO 4
<211> LENGTH: 200
<212> TYPE: DNA
<213> ORGANISM: Artificial Sequence
<220> FEATURE:
<223> OTHER INFORMATION: synthetic

<400> SEQUENCE: 4
gccaggggga ggtgacttac caggcaggag gcacagccgc cctagctctg atgttgacct            60
ttccctcggg ctcttctctt cataggcctt gcctctggga tccccacgct gtgacctgaa           120
ggagaacctg ctgaaggaca attgtgctcc agagtctatt gagttcccag tcagtgaggc           180
ccagatcctg gaggctaggc                                                      200

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
aaccatggaa ggaccatgac                                                        20

<210> SEQ ID NO 6
<211> LENGTH: 18
<212> TYPE: DNA
<213> ORGANISM: Artificial Sequence
<220> FEATURE:
<223> OTHER INFORMATION: synthetic

<400> SEQUENCE: 6
caccccagtc ctatcctg                                                          18

-continued

```
<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
ctcctcagag cactcacaca                                                  20

<210> SEQ ID NO 8
<211> LENGTH: 166
<212> TYPE: DNA
<213> ORGANISM: Artificial Sequence
<220> FEATURE:
<223> OTHER INFORMATION: synthetic

<400> SEQUENCE: 8
agccttccag cccacgctgc aacaatggga acgggacttt tgagtgtggg gtgtgccgct      60
gtgaccaggg ctggctgggg tcccaatgcg agtgctctga ggaggattac cgaccctctc    120
agcaggaaga gtgcagcccc aaggagggcc agcccatctg cagcca                   166

<210> SEQ ID NO 9
<211> LENGTH: 29
<212> TYPE: DNA
<213> ORGANISM: Artificial Sequence
<220> FEATURE:
<223> OTHER INFORMATION: synthetic

<400> SEQUENCE: 9
gagaaggagc agtctttcac tatcaagcc                                        29

<210> SEQ ID NO 10
<211> LENGTH: 23
<212> TYPE: DNA
<213> ORGANISM: Artificial Sequence
<220> FEATURE:
<223> OTHER INFORMATION: synthetic

<400> SEQUENCE: 10
gcaggagaag tcatcgcact cac                                              23

<210> SEQ ID NO 11
<211> LENGTH: 39
<212> TYPE: DNA
<213> ORGANISM: Artificial Sequence
<220> FEATURE:
<223> OTHER INFORMATION: synthetic

<400> SEQUENCE: 11
gtgctcagat gaggccttgc ctctgggctc accccgatg                             39

<210> SEQ ID NO 12
<211> LENGTH: 39
<212> TYPE: DNA
<213> ORGANISM: Artificial Sequence
<220> FEATURE:
<223> OTHER INFORMATION: synthetic

<400> SEQUENCE: 12
catcggggtg agcccagagg caaggcctca tctgagcac                             39
```

<210> SEQ ID NO 13
<211> LENGTH: 34
<212> TYPE: DNA
<213> ORGANISM: Artificial Sequence
<220> FEATURE:
<223> OTHER INFORMATION: synthetic

<400> SEQUENCE: 13
gggctcaccc cgatgtgacc tgaaggagaa cctg              34

<210> SEQ ID NO 14
<211> LENGTH: 34
<212> TYPE: DNA
<213> ORGANISM: Artificial Sequence
<220> FEATURE:
<223> OTHER INFORMATION: synthetic

<400> SEQUENCE: 14
caggttctcc ttcaggtcac atcggggtga gccc              34

<210> SEQ ID NO 15
<211> LENGTH: 43
<212> TYPE: DNA
<213> ORGANISM: Artificial Sequence
<220> FEATURE:
<223> OTHER INFORMATION: synthetic

<400> SEQUENCE: 15
gaccagggct ggctggggtc ccagtgtgag tgctctgagg agg              43

<210> SEQ ID NO 16
<211> LENGTH: 43
<212> TYPE: DNA
<213> ORGANISM: Artificial Sequence
<220> FEATURE:
<223> OTHER INFORMATION: synthetic

<400> SEQUENCE: 16
cctcctcaga gcactcacac tgggacccca gccagccctg gtc              43

<210> SEQ ID NO 17
<211> LENGTH: 32
<212> TYPE: DNA
<213> ORGANISM: Artificial Sequence
<220> FEATURE:
<223> OTHER INFORMATION: synthetic

<400> SEQUENCE: 17
gaccccagcc agccagggcc acagcggcac ac              32

<210> SEQ ID NO 18
<211> LENGTH: 34
<212> TYPE: DNA
<213> ORGANISM: Artificial Sequence
<220> FEATURE:
<223> OTHER INFORMATION: synthetic

<400> SEQUENCE: 18
ggtgtgccgc tgtggccctg gctggctggg gtcc              34

<210> SEQ ID NO 19
<211> LENGTH: 45
<212> TYPE: DNA
<213> ORGANISM: Artificial Sequence
<220> FEATURE:
<223> OTHER INFORMATION: synthetic

<400> SEQUENCE: 19
gggcctggct ggctgggatc catgtgtgag tgctcagagg aggac                45

<210> SEQ ID NO 20
<211> LENGTH: 45
<212> TYPE: DNA
<213> ORGANISM: Artificial Sequence
<220> FEATURE:
<223> OTHER INFORMATION: synthetic

<400> SEQUENCE: 20
gtcctcctct gagcactcac acatggatcc cagccagcca ggccc                45

<210> SEQ ID NO 21
<211> LENGTH: 31
<212> TYPE: DNA
<213> ORGANISM: Artificial Sequence
<220> FEATURE:
<223> OTHER INFORMATION: synthetic

<400> SEQUENCE: 21
ctgaacctaa tagccctcgc tgcaacaatg g                                31

<210> SEQ ID NO 22
<211> LENGTH: 31
<212> TYPE: DNA
<213> ORGANISM: Artificial Sequence
<220> FEATURE:
<223> OTHER INFORMATION: synthetic

<400> SEQUENCE: 22
ccattgttgc agcgagggct attaggttca g                                31

<210> SEQ ID NO 23
<211> LENGTH: 41
<212> TYPE: DNA
<213> ORGANISM: Artificial Sequence
<220> FEATURE:
<223> OTHER INFORMATION: synthetic

<400> SEQUENCE: 23
gtggggtatg ccgttgtgac cagggctggc tgggatccca g                     41

<210> SEQ ID NO 24
<211> LENGTH: 41
<212> TYPE: DNA
<213> ORGANISM: Artificial Sequence
<220> FEATURE:
<223> OTHER INFORMATION: synthetic

<400> SEQUENCE: 24
ctgggatccc agccagccct ggtcacaacg gcatacccca c                     41

<210> SEQ ID NO 25
<211> LENGTH: 762
<212> TYPE: PRT
<213> ORGANISM: Mus musculus

<400> SEQUENCE: 25

Glu Ser Asn Ile Cys Thr Thr Arg Gly Val Asn Ser Cys Gln Gln Cys
1               5                   10                  15

Leu Ala Val Ser Pro Val Cys Ala Trp Cys Ser Asp Glu Thr Leu Ser
            20                  25                  30

```
Gln Gly Ser Pro Arg Cys Asn Leu Lys Glu Asn Leu Leu Lys Asp Asn
         35                  40                  45

Cys Ala Pro Glu Ser Ile Glu Phe Pro Val Ser Glu Ala Gln Ile Leu
 50                  55                  60

Glu Ala Arg Pro Leu Ser Ser Lys Gly Ser Gly Ser Ser Ala Gln Ile
 65                  70                  75                  80

Thr Gln Val Ser Pro Gln Arg Ile Ala Leu Arg Leu Arg Pro Asp Asp
                 85                  90                  95

Ser Lys Ile Phe Ser Leu Gln Val Arg Gln Val Glu Asp Tyr Pro Val
                100                 105                 110

Asp Ile Tyr Tyr Leu Met Asp Leu Ser Phe Ser Met Lys Asp Asp Leu
             115                 120                 125

Ser Ser Ile Gln Thr Leu Gly Thr Lys Leu Ala Ser Gln Met Arg Lys
     130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Gln Ala Ile Lys Asn Pro
                165                 170                 175

Cys Tyr Asn Met Lys Asn Ala Cys Leu Pro Met Phe Gly Tyr Lys His
             180                 185                 190

Val Leu Thr Leu Thr Asp Gln Val Ser Arg Phe Asn Glu Glu Val Lys
     195                 200                 205

Lys Gln Ser Val Ser Arg Asn Arg Asp Ala Pro Glu Gly Gly Phe Asp
                210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Leu Pro Asn Asp Gly His
             260                 265                 270

Cys His Ile Gly Thr Asp Asn His Tyr Ser Ala Ser Thr Thr Met Asp
     275                 280                 285

Tyr Pro Ser Leu Gly Leu Met Thr Glu Lys Leu Ser Gln Lys Asn Ile
290                 295                 300

Asn Leu Ile Phe Ala Val Thr Glu Asn Val Val Ser Leu Tyr Gln Asn
305                 310                 315                 320

Tyr Ser Glu Leu Ile Pro Gly Thr Thr Val Gly Val Leu Ser Asp Asp
                325                 330                 335

Ser Ser Asn Val Leu Gln Leu Ile Val Asp Ala Tyr Gly Lys Ile Arg
             340                 345                 350

Ser Lys Val Glu Leu Glu Val Arg Asp Leu Pro Glu Glu Leu Ser Leu
     355                 360                 365

Ser Phe Asn Ala Thr Cys Leu Asn Asn Glu Val Ile Pro Gly Leu Lys
     370                 375                 380

Ser Cys Val Gly Leu Lys Ile Gly Asp Thr Val Ser Phe Ser Ile Glu
385                 390                 395                 400

Ala Lys Val Arg Gly Cys Pro Gln Glu Lys Glu Gln Ser Phe Thr Ile
                405                 410                 415

Lys Pro Val Gly Phe Lys Asp Ser Leu Thr Val Gln Val Thr Phe Asp
             420                 425                 430

Cys Asp Cys Ala Cys Gln Ala Phe Ala Gln Pro Ser Ser Pro Arg Cys
     435                 440                 445
```

```
Asn Asn Gly Asn Gly Thr Phe Glu Cys Gly Val Cys Arg Cys Asp Gln
    450                 455                 460

Gly Trp Leu Gly Ser Met Cys Glu Cys Ser Glu Glu Asp Tyr Arg Pro
465                 470                 475                 480

Ser Gln Gln Glu Cys Ser Pro Lys Glu Gly Gln Pro Ile Cys Ser
            485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
            515                 520                 525

Val Arg Tyr Lys Gly Glu Met Cys Ser Gly His Gly Gln Cys Asn Cys
530                 535                 540

Gly Asp Cys Val Cys Asp Ser Asp Trp Thr Gly Tyr Tyr Cys Asn Cys
545                 550                 555                 560

Thr Thr Arg Thr Asp Thr Cys Met Ser Thr Asn Gly Leu Leu Cys Ser
                565                 570                 575

Gly Arg Gly Asn Cys Glu Cys Gly Ser Cys Val Cys Val Gln Pro Gly
            580                 585                 590

Ser Tyr Gly Asp Thr Cys Glu Lys Cys Pro Thr Cys Pro Asp Ala Cys
            595                 600                 605

Ser Phe Lys Lys Glu Cys Val Glu Cys Lys Lys Phe Asn Arg Gly Thr
    610                 615                 620

Leu His Glu Glu Asn Thr Cys Ser Arg Tyr Cys Arg Asp Asp Ile Glu
625                 630                 635                 640

Gln Val Lys Glu Leu Thr Asp Thr Gly Lys Asn Ala Val Asn Cys Thr
                645                 650                 655

Tyr Lys Asn Glu Asp Asp Cys Val Val Arg Phe Gln Tyr Tyr Glu Asp
            660                 665                 670

Thr Ser Gly Arg Ala Val Leu Tyr Val Val Glu Glu Pro Glu Cys Pro
            675                 680                 685

Lys Gly Pro Asp Ile Leu Val Val Leu Leu Ser Val Met Gly Ala Ile
    690                 695                 700

Leu Leu Ile Gly Leu Ala Thr Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
            755                 760

<210> SEQ ID NO 26
<211> LENGTH: 762
<212> TYPE: PRT
<213> ORGANISM: Artificial Sequence
<220> FEATURE:
<223> OTHER INFORMATION: synthetic

<400> SEQUENCE: 26

Glu Ser Asn Ile Cys Thr Thr Arg Gly Val Asn Ser Cys Gln Gln Cys
1               5                   10                  15

Leu Ala Val Ser Pro Val Cys Ala Trp Cys Ser Asp Glu Ala Leu Pro
                20                  25                  30

Leu Gly Ser Pro Arg Cys Asp Leu Lys Glu Asn Leu Leu Lys Asp Asn
            35                  40                  45
```

```
Cys Ala Pro Glu Ser Ile Glu Phe Pro Val Ser Glu Ala Gln Ile Leu
 50                  55                  60

Glu Ala Arg Pro Leu Ser Ser Lys Gly Ser Gly Ser Ser Ala Gln Ile
 65                  70                  75                  80

Thr Gln Val Ser Pro Gln Arg Ile Ala Leu Arg Leu Arg Pro Asp Asp
                     85                  90                  95

Ser Lys Ile Phe Ser Leu Gln Val Arg Gln Val Glu Asp Tyr Pro Val
                100                 105                 110

Asp Ile Tyr Tyr Leu Met Asp Leu Ser Phe Ser Met Lys Asp Asp Leu
            115                 120                 125

Ser Ser Ile Gln Thr Leu Gly Thr Lys Leu Ala Ser Gln Met Arg Lys
130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Gln Ala Ile Lys Asn Pro
                165                 170                 175

Cys Tyr Asn Met Lys Asn Ala Cys Leu Pro Met Phe Gly Tyr Lys His
            180                 185                 190

Val Leu Thr Leu Thr Asp Gln Val Ser Arg Phe Asn Glu Glu Val Lys
            195                 200                 205

Lys Gln Ser Val Ser Arg Asn Arg Asp Ala Pro Glu Gly Gly Phe Asp
210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Leu Pro Asn Asp Gly His
            260                 265                 270

Cys His Ile Gly Thr Asp Asn His Tyr Ser Ala Ser Thr Thr Met Asp
            275                 280                 285

Tyr Pro Ser Leu Gly Leu Met Thr Glu Lys Leu Ser Gln Lys Asn Ile
290                 295                 300

Asn Leu Ile Phe Ala Val Thr Glu Asn Val Val Ser Leu Tyr Gln Asn
305                 310                 315                 320

Tyr Ser Glu Leu Ile Pro Gly Thr Thr Val Gly Val Leu Ser Asp Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu
            355                 360                 365

Ser Phe Asn Ala Thr Cys Leu Asn Asn Glu Val Ile Pro Gly Leu Lys
370                 375                 380

Ser Cys Val Gly Leu Lys Ile Gly Asp Thr Val Ser Phe Ser Ile Glu
385                 390                 395                 400

Ala Lys Val Arg Gly Cys Pro Gln Glu Lys Glu Gln Ser Phe Thr Ile
                405                 410                 415

Lys Pro Val Gly Phe Lys Asp Ser Leu Thr Val Gln Val Thr Phe Asp
            420                 425                 430

Cys Asp Cys Ala Cys Gln Ala Phe Ala Gln Pro Ser Ser Pro Arg Cys
            435                 440                 445

Asn Asn Gly Asn Gly Thr Phe Glu Cys Gly Val Cys Arg Cys Asp Gln
450                 455                 460
```

```
Gly Trp Leu Gly Ser Gln Cys Glu Cys Ser Glu Asp Tyr Arg Pro
465                 470                 475                 480

Ser Gln Gln Glu Glu Cys Ser Pro Lys Glu Gly Gln Pro Ile Cys Ser
                485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
        515                 520                 525

Val Arg Tyr Lys Gly Glu Met Cys Ser Gly His Gly Gln Cys Asn Cys
530                 535                 540

Gly Asp Cys Val Cys Asp Ser Asp Trp Thr Gly Tyr Tyr Cys Asn Cys
545                 550                 555                 560

Thr Thr Arg Thr Asp Thr Cys Met Ser Thr Asn Gly Leu Leu Cys Ser
                565                 570                 575

Gly Arg Gly Asn Cys Glu Cys Gly Ser Cys Val Cys Val Gln Pro Gly
            580                 585                 590

Ser Tyr Gly Asp Thr Cys Glu Lys Cys Pro Thr Cys Pro Asp Ala Cys
        595                 600                 605

Ser Phe Lys Lys Glu Cys Val Glu Cys Lys Lys Phe Asn Arg Gly Thr
610                 615                 620

Leu His Glu Glu Asn Thr Cys Ser Arg Tyr Cys Arg Asp Asp Ile Glu
625                 630                 635                 640

Gln Val Lys Glu Leu Thr Asp Thr Gly Lys Asn Ala Val Asn Cys Thr
                645                 650                 655

Tyr Lys Asn Glu Asp Asp Cys Val Val Arg Phe Gln Tyr Tyr Glu Asp
            660                 665                 670

Thr Ser Gly Arg Ala Val Leu Tyr Val Val Glu Glu Pro Glu Cys Pro
        675                 680                 685

Lys Gly Pro Asp Ile Leu Val Val Leu Leu Ser Val Met Gly Ala Ile
690                 695                 700

Leu Leu Ile Gly Leu Ala Thr Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
        755                 760

<210> SEQ ID NO 27
<211> LENGTH: 762
<212> TYPE: PRT
<213> ORGANISM: Artificial Sequence
<220> FEATURE:
<223> OTHER INFORMATION: synthetic

<400> SEQUENCE: 27

Glu Ser Asn Ile Cys Thr Thr Arg Gly Val Asn Ser Cys Gln Gln Cys
1               5                   10                  15

Leu Ala Val Ser Pro Met Cys Ala Trp Cys Ser Asp Glu Ala Leu Pro
                20                  25                  30

Leu Gly Ser Pro Arg Cys Asp Leu Lys Glu Asn Leu Leu Lys Asp Asn
            35                  40                  45

Cys Ala Pro Glu Ser Ile Glu Phe Pro Val Ser Glu Ala Gln Ile Leu
        50                  55                  60
```

-continued

```
Glu Ala Arg Pro Leu Ser Ser Lys Gly Ser Gly Ser Ala Gln Ile
 65                  70                  75                  80

Thr Gln Val Ser Pro Gln Arg Ile Ala Leu Arg Leu Arg Pro Asp Asp
                 85                  90                  95

Ser Lys Ile Phe Ser Leu Gln Val Arg Gln Val Glu Asp Tyr Pro Val
                100                 105                 110

Asp Ile Tyr Tyr Leu Met Asp Leu Ser Phe Ser Met Lys Asp Asp Leu
                115                 120                 125

Ser Ser Ile Gln Thr Leu Gly Thr Lys Leu Ala Ser Gln Met Arg Lys
130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Gln Ala Ile Lys Asn Pro
                165                 170                 175

Cys Tyr Asn Met Lys Asn Ala Cys Leu Pro Met Phe Gly Tyr Lys His
                180                 185                 190

Val Leu Thr Leu Thr Asp Gln Val Ser Arg Phe Asn Glu Glu Val Lys
                195                 200                 205

Lys Gln Ser Val Ser Arg Asn Arg Asp Ala Pro Glu Gly Gly Phe Asp
210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Leu Pro Asn Asp Gly His
                260                 265                 270

Cys His Ile Gly Thr Asp Asn His Tyr Ser Ala Ser Thr Thr Met Asp
                275                 280                 285

Tyr Pro Ser Leu Gly Leu Met Thr Glu Lys Leu Ser Gln Lys Asn Ile
                290                 295                 300

Asn Leu Ile Phe Ala Val Thr Glu Asn Val Val Ser Leu Tyr Gln Asn
305                 310                 315                 320

Tyr Ser Glu Leu Ile Pro Gly Thr Thr Val Gly Val Leu Ser Asp Asp
                325                 330                 335

Ser Ser Asn Val Leu Gln Leu Ile Val Asp Ala Tyr Gly Lys Ile Arg
                340                 345                 350

Ser Lys Val Glu Leu Glu Val Arg Asp Leu Pro Glu Glu Leu Ser Leu
                355                 360                 365

Ser Phe Asn Ala Thr Cys Leu Asn Asn Glu Val Ile Pro Gly Leu Lys
370                 375                 380

Ser Cys Val Gly Leu Lys Ile Gly Asp Thr Val Ser Phe Ser Ile Glu
385                 390                 395                 400

Ala Lys Val Arg Gly Cys Pro Gln Glu Lys Glu Gln Ser Phe Thr Ile
                405                 410                 415

Lys Pro Val Gly Phe Lys Asp Ser Leu Thr Val Gln Val Thr Phe Asp
                420                 425                 430

Cys Asp Cys Ala Cys Gln Ala Phe Ala Gln Pro Ser Ser Pro Arg Cys
                435                 440                 445

Asn Asn Gly Asn Gly Thr Phe Glu Cys Gly Val Cys Arg Cys Asp Gln
                450                 455                 460

Gly Trp Leu Gly Ser Gln Cys Glu Cys Ser Glu Glu Asp Tyr Arg Pro
465                 470                 475                 480
```

-continued

```
Ser Gln Gln Glu Glu Cys Ser Pro Lys Glu Gly Gln Pro Ile Cys Ser
                485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Phe Ser Cys
        515                 520                 525

Val Arg Tyr Lys Gly Glu Met Cys Ser Gly His Gly Gln Cys Asn Cys
    530                 535                 540

Gly Asp Cys Val Cys Asp Ser Asp Trp Thr Gly Tyr Tyr Cys Asn Cys
545                 550                 555                 560

Thr Thr Arg Thr Asp Thr Cys Met Ser Thr Asn Gly Leu Leu Cys Ser
                565                 570                 575

Gly Arg Gly Asn Cys Glu Cys Gly Ser Cys Val Cys Val Gln Pro Gly
            580                 585                 590

Ser Tyr Gly Asp Thr Cys Glu Lys Cys Pro Thr Cys Pro Asp Ala Cys
        595                 600                 605

Ser Phe Lys Lys Glu Cys Val Glu Cys Lys Lys Phe Asn Arg Gly Thr
    610                 615                 620

Leu His Glu Glu Asn Thr Cys Ser Arg Tyr Cys Arg Asp Asp Ile Glu
625                 630                 635                 640

Gln Val Lys Glu Leu Thr Asp Thr Gly Lys Asn Ala Val Asn Cys Thr
                645                 650                 655

Tyr Lys Asn Glu Asp Asp Cys Val Val Arg Phe Gln Tyr Tyr Glu Asp
            660                 665                 670

Thr Ser Gly Arg Ala Val Leu Tyr Val Val Glu Glu Pro Glu Cys Pro
        675                 680                 685

Lys Gly Pro Asp Ile Leu Val Val Leu Leu Ser Val Met Gly Ala Ile
    690                 695                 700

Leu Leu Ile Gly Leu Ala Thr Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
        755                 760
```

<210> SEQ ID NO 28
<211> LENGTH: 18
<212> TYPE: PRT
<213> ORGANISM: Artificial Sequence
<220> FEATURE:
<223> OTHER INFORMATION: synthetic

<400> SEQUENCE: 28

```
Met Cys Ala Trp Cys Ser Asp Glu Ala Leu Pro Leu Gly Ser Pro Arg
1               5                   10                  15

Cys Asp
```

<210> SEQ ID NO 29
<211> LENGTH: 62
<212> TYPE: DNA
<213> ORGANISM: Mus musculus

<400> SEQUENCE: 29
ctcttctctt catagacttt gtctcagggc tcaccccgat gtaacctgaa ggagaacctg        60
ct                                                                      62

<210> SEQ ID NO 30
<211> LENGTH: 62
<212> TYPE: DNA
<213> ORGANISM: Mus musculus

<400> SEQUENCE: 30
agcaggttct ccttcaggtt acatcggggt gagccctgag acaaagtcta tgaagagaag        60
ag                                                                      62

<210> SEQ ID NO 31
<211> LENGTH: 10
<212> TYPE: PRT
<213> ORGANISM: Mus musculus

<400> SEQUENCE: 31

Thr Leu Ala Gln Gly Ser Pro Arg Cys Asn
1               5                   10

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

Ala Leu Pro Leu Gly Ser Pro Arg Cys Asp
1               5                   10

<210> SEQ ID NO 33
<211> LENGTH: 33
<212> TYPE: DNA
<213> ORGANISM: Artificial Sequence
<220> FEATURE:
<223> OTHER INFORMATION: synthetic

<400> SEQUENCE: 33
aggcgttgcc tctgggatcc ccacgatgtg acc                                    33

<210> SEQ ID NO 34
<211> LENGTH: 33
<212> TYPE: DNA
<213> ORGANISM: Artificial Sequence
<220> FEATURE:
<223> OTHER INFORMATION: synthetic

<400> SEQUENCE: 34
agactttgtc tcagggctca ccccgatgta acc                                    33

<210> SEQ ID NO 35
<211> LENGTH: 33
<212> TYPE: DNA
<213> ORGANISM: Artificial Sequence
<220> FEATURE:
<223> OTHER INFORMATION: synthetic

<400> SEQUENCE: 35
aggcgttgcc tctgggatcc ccacgctgtg acc                                    33

<210> SEQ ID NO 36
<211> LENGTH: 57
<212> TYPE: PRT
<213> ORGANISM: Homo sapiens

<400> SEQUENCE: 36

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45

Cys Ala Pro Glu Ser Ile Glu Phe Pro
    50                  55

<210> SEQ ID NO 37
<211> LENGTH: 57
<212> TYPE: PRT
<213> ORGANISM: Mus musculus

<400> SEQUENCE: 37

Glu Ser Asn Ile Cys Thr Thr Arg Gly Val Asn Ser Cys Gln Gln Cys
1               5                   10                  15

Leu Ala Val Ser Pro Val Cys Ala Trp Cys Ser Asp Glu Thr Leu Ser
            20                  25                  30

Gln Gly Ser Pro Arg Cys Asn Leu Lys Glu Asn Leu Leu Lys Asp Asn
        35                  40                  45

Cys Ala Pro Glu Ser Ile Glu Phe Pro
    50                  55

<210> SEQ ID NO 38
<211> LENGTH: 40
<212> TYPE: PRT
<213> ORGANISM: Homo sapiens

<400> SEQUENCE: 38

Cys Asp Cys Ala Cys Gln Ala Gln Ala Glu Pro Asn Ser His Arg Cys
1               5                   10                  15

Asn Asn Gly Asn Gly Thr Phe Glu Cys Gly Val Cys Arg Cys Gly Pro
            20                  25                  30

Gly Trp Leu Gly Ser Gln Cys Glu
        35                  40

<210> SEQ ID NO 39
<211> LENGTH: 40
<212> TYPE: PRT
<213> ORGANISM: Mus musculus

<400> SEQUENCE: 39

Cys Asp Cys Ala Cys Gln Ala Phe Ala Gln Pro Ser Ser Pro Arg Cys
1               5                   10                  15

Asn Asn Gly Asn Gly Thr Phe Glu Cys Gly Val Cys Arg Cys Asp Gln
            20                  25                  30

Gly Trp Leu Gly Ser Met Cys Glu
        35                  40

<210> SEQ ID NO 40
<211> LENGTH: 50
<212> TYPE: DNA
<213> ORGANISM: Mus musculus

<400> SEQUENCE: 40
ccagggctgg ctggggtcca tgtgtgagtg ctctgaggag gattaccgac          50

<210> SEQ ID NO 41
<211> LENGTH: 50
<212> TYPE: DNA
<213> ORGANISM: Mus musculus

<400> SEQUENCE: 41
gtcggtaatc ctcctcagag cactcacaca tggacccccag ccagccctgg         50

<210> SEQ ID NO 42
<211> LENGTH: 4
<212> TYPE: PRT
<213> ORGANISM: Mus musculus

<400> SEQUENCE: 42

Ser Met Cys Glu
1

<210> SEQ ID NO 43
<211> LENGTH: 4
<212> TYPE: PRT
<213> ORGANISM: Artificial Sequence
<220> FEATURE:
<223> OTHER INFORMATION: synthetic

<400> SEQUENCE: 43

Ser Gln Cys Glu
1

<210> SEQ ID NO 44
<211> LENGTH: 12
<212> TYPE: DNA
<213> ORGANISM: Artificial Sequence
<220> FEATURE:
<223> OTHER INFORMATION: synthetic

<400> SEQUENCE: 44
tcccaatgcg ag                                                   12

<210> SEQ ID NO 45
<211> LENGTH: 10
<212> TYPE: PRT
<213> ORGANISM: Mus musculus

<400> SEQUENCE: 45

Trp Leu Gly Ser Met Cys Glu Cys Ser Glu
1               5                   10

<210> SEQ ID NO 46
<211> LENGTH: 33
<212> TYPE: DNA
<213> ORGANISM: Mus musculus

<400> SEQUENCE: 46
gctggctggg gtccatgtgt gagtgctctg agg                            33

<210> SEQ ID NO 47
<211> LENGTH: 10
<212> TYPE: PRT
<213> ORGANISM: Artificial Sequence
<220> FEATURE:
<223> OTHER INFORMATION: synthetic

```
<400> SEQUENCE: 47

Trp Leu Gly Ser Gln Cys Glu Cys Ser Glu
1               5                   10

<210> SEQ ID NO 48
<211> LENGTH: 33
<212> TYPE: DNA
<213> ORGANISM: Artificial Sequence
<220> FEATURE:
<223> OTHER INFORMATION: synthetic

<400> SEQUENCE: 48
gctggctggg gtcccaatgc gagtgctctg agg                                    33
```

MURINE MODEL OF FETAL/NEONATAL ALLOIMMUNE THROMBOCYTOPENIA

STATEMENT REGARDING FEDERALLY SPONSORED RESEARCH

This invention was made with government support under R01HL130054 and R35HL139937 awarded by the National Institutes of Health. The government has certain rights in this invention.

CROSS-REFERENCE TO RELATED APPLICATIONS

Not applicable.

REFERENCE TO A SEQUENCE LISTING SUBMITTED VIA EFS-WEB

The content of the ASCII text file of the sequence listing named "160180_00134_ST25.txt" which is 29.0 kb in size was created on Nov. 4, 2019 and electronically submitted via EFS-Web herewith the application is incorporated herein by reference in its entirety.

BACKGROUND

Alloantibodies to platelet-specific antigens are responsible for three clinically-important bleeding disorders: Post-transfusion purpura (PTP), refractoriness to platelet transfusion (RPT) and fetal/neonatal alloimmune thrombocytopenia (FNAIT—variously referred to in the literature as NATP or NAIT—see reference[1] for a review). PTP is a rare syndrome in which a multiparous woman, after receiving a blood transfusion, enigmatically clears not only the transfused platelets, but her own as well, leading to severe thrombocytopenia, bruising, and petechiae. RPT is seen in patients who are multiply transfused with platelets and remains a clinical challenge, resulting in bleeding complications and lengthened hospitalization. RPT can be separated into immune and non-immune causes. Immune causes include alloimmunization to HLA and/or platelet-specific antigens due to prior exposure from pregnancy, transfusions and/or transplantation. Non-immune causes, based on studies in patients with acute myeloid leukaemia (AML) or haematopoietic progenitor cell transplants, include fever, sepsis, splenomegaly, disseminated intravascular coagulation (DIC), bleeding, venoocclusive disease (VOD), graft-versus-host disease (GVHD) and medications[54]. Unlike PTP or RPT, FNAIT is a fairly common disorder, leading to severe fetal and/or neonatal thrombocytopenia in approximately 1 in 1000 to 1 in 2000 live births[2,3]. Although many infants recover uneventfully, FNAIT is a leading cause of severe thrombocytopenia in the fetus and neonate, with nearly half experiencing bleeding serious enough to require transfusion with "antigen-negative" platelets[4]. The most destructive consequences of FNAIT, however, are intracranial hemorrhage and intrauterine death as early as 20-24 weeks of gestation[2,5,6]. Despite advances in treatment, FNAIT remains a leading cause of intracranial hemorrhage in full-term infants[4,7-10], often leading to life-long disability.

Work performed in many laboratories over the past 60 years has led to the identification of more than 30 distinct heritable Human Platelet-specific Alloantigen (HPA) systems (HPAs 1-30), located on five different glycoproteins, currently recognized by the Platelet Nomenclature Committee of the International Society of Blood Transfusion (ISBT) and the ISTH[11]. Of these, the HPA-1a (also known as Pl$^{A1}$) epitope is the one that most commonly provokes PTP and FNAIT, being responsible for ~80% of the cases in which an alloantibody can be detected[12], and has accordingly been the most extensively studied. However, a need in the art exists for improved models for studying the HPA-1a/1b epitope and improved diagnostic, prophylactic, and treatment methods for PTP and FNAIT.

SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and any and all such combinations of embodiments are intended to fall within the scope of the present invention.

In a first aspect, provided herein is a transgenic mouse whose genome comprises a nucleic acid encoding a variant platelet membrane glycoprotein IIIc (GPIIIa) having at least 95% identity to SEQ ID NO: 25, wherein the variant GPIIIa comprises mutations T30A, S32P, Q33L, N39D, and M470Q in SEQ ID NO: 25. In some embodiments, the mouse expresses a variant GPIIIa comprising the sequence set forth in SEQ ID NO:26. In some embodiments, the variant GPIIIa further comprises mutation V22M relative to SEQ ID NO: 25. In some embodiments, the variant GPIIIa can bind to an anti-HPA-1a antibody.

In a second aspect, provided herein is an in vitro method of identifying a molecule that is able to specifically bind to a variant platelet membrane glycoprotein IIIc (GPIIIa), the method comprising: contacting a candidate molecule with platelets from a transgenic mouse described herein; and determining whether the candidate molecule binds to the platelets; wherein the candidate molecule is able to specifically bind to the variant GPIIIa if the candidate molecule binds to the platelets from the transgenic mouse but does not bind to platelets from a wild-type mouse. In some embodiments, the candidate molecule is selected from the group consisting of an antibody, an Fv, an F(ab), a F(ab'), F(ab')$_2$, and a single chain form of any of the foregoing.

In a third aspect, provided herein is an in vivo method of identifying a molecule that is able to prevent an anti-HPA-1a alloimmune response in a female mouse, the method comprising: administering to a test mouse a candidate molecule, wherein the test mouse is pregnant with pups heterozygous for wild-type platelet membrane glycoprotein IIIc (GPIIIa) and a variant GPIIIa comprising mutations T30A, S32P, Q33L, N39D, and M470Q relative to SEQ ID NO:25, and wherein the test mouse is negative for anti-HPA-1a antibodies; and measuring anti-HPA-1a antibody titer in the test mouse; wherein the candidate molecule is able to prevent an anti-HPA-1a alloimmune response if the anti-HPA-1a antibody titer in the test mouse, measured by single antigen bead assay, is undetectable at two weeks postpartum. In some embodiments, the anti-HPA-1a antibody titer in the test mouse is undetectable at six weeks postpartum. In some embodiments, the candidate molecule is selected from the group consisting of an antibody, an Fv, an F(ab), a F(ab'), F(ab')$_2$, and a single chain form of any of the foregoing.

In a fourth aspect, provided herein is an in vivo method of identifying a molecule that is able to inhibit an anti-HPA-1a alloantibody from binding to fetal or neonatal platelets, the method comprising: administering to a test mouse a candidate molecule, wherein the test mouse pregnant with pups heterozygous for wild-type platelet membrane glycoprotein IIIc (GPIIIa) and a variant GPIIIa comprising mutations T30A, S32P, Q33L, N39D, and M470Q relative to SEQ ID NO:25, and wherein the test mouse was immunized prior to pregnancy with (i) platelets from a transgenic mouse of described herein or (ii) a variant GPIIIa comprising mutations T30A, S32P, Q33L, N39D, and M470Q relative to SEQ ID NO:25; and measuring fetal or neonatal platelet count; wherein the candidate molecule is able to inhibit an anti-HPA-1a alloantibody from binding to fetal or neonatal platelets if the fetal or neonatal platelet count in pups of the test mouse is higher than the fetal or neonatal platelet count in pups of a control mouse. In some embodiments, bleeding is reduced or prevented in pups of the test mouse, compared with pups of a control mouse. In some embodiments, the candidate molecule is selected from the group consisting of an antibody, an Fv, an F(ab), a F(ab'), F(ab')$_2$, and a single chain form of any of the foregoing.

In a fifth aspect, provided herein is an in vivo method of identifying a molecule that is able to inhibit an anti-HPA-1a alloantibody from crossing the placenta of a pregnant mouse, the method comprising: administering to a test mouse a candidate molecule, wherein the test mouse pregnant with pups heterozygous for wild-type platelet membrane glycoprotein IIIc (GPIIIa) and a variant GPIIIa comprising mutations T30A, S32P, Q33L, N39D, and M470Q relative to SEQ ID NO:25, and wherein the test mouse was immunized prior to pregnancy with (i) platelets from a transgenic mouse described herein or (ii) a variant GPIIIa comprising mutations T30A, S32P, Q33L, N39D, and M470Q relative to SEQ ID NO:25; and measuring fetal or neonatal anti-HPA-1a antibody titer; wherein the candidate molecule is able to inhibit an anti-HPA-1a alloantibody from crossing the placenta of the pregnant mouse if the fetal or neonatal antibody titer in pups of the test mouse is lower than the fetal or neonatal antibody titer in pups of a control mouse. In some embodiments, bleeding is reduced or prevented in pups of the test mouse, compared with pups of a control mouse. In some embodiments, the candidate molecule is selected from the group consisting of an antibody, an Fv, an F(ab), a F(ab'), F(ab')$_2$, and a single chain form of any of the foregoing.

In a sixth aspect, provided herein is a variant platelet membrane glycoprotein IIIa (GPIIIa) comprising the amino acid sequence set forth in SEQ ID NO: 26.

In a seventh aspect, provided herein is an in vitro method of identifying a molecule that is able to compete with an anti-HPA-1a antibody for binding to a variant GPIIIa described herein, the method comprising: contacting the variant GPIIIa with the anti-HPA-1a antibody to form a GPIIIa-antibody complex, wherein the variant GPIIIa is immobilized on a substrate and wherein the anti-HPA-1a antibody comprises a label; contacting the GPIIIa-antibody complex with a candidate molecule in solution; and determining whether the candidate molecule competes for anti-HPA-1a antibody binding to the variant GPIIIa by detecting the amount of label on the substrate or in the solution; wherein the candidate molecule is able to compete with the anti-HPA-1a antibody for binding to the variant GPIIIa if the amount of label detected on the substrate is reduced after contacting the GPIIIa-antibody complex with the candidate molecule compared with the amount of label detected on the substrate before contacting the GPIIIa-antibody complex with the candidate molecule; or wherein the candidate molecule is able to compete with the anti-HPA-1a antibody for binding to the variant GPIIIa if the amount of label in the solution is increased after contacting the GPIIIa-antibody complex with the candidate molecule compared with the amount of label in the solution before contacting the GPIIIa-antibody complex with the candidate molecule. In some embodiments, the anti-HPA-1a antibody is monoclonal antibody 26.4. In some embodiments, the label is selected from the group consisting of a fluorophore, a radioisotope, a chemiluminescent probe, and a bioluminescent probe. In some embodiments, the substrate is selected from the group consisting of a bead, a resin, a particle, a membrane, and a gel. In some embodiments, the candidate molecule is selected from the group consisting of an antibody, an Fv, an F(ab), a F(ab'), F(ab')$_2$, and a single chain form of any of the foregoing.

In an eight aspect, provided herein is a method for making a transgenic mouse described herein, the method comprising: injecting into the cytoplasm of a fertilized murine oocyte i) a Cas9 nuclease or a nucleotide encoding a Cas9 nuclease; ii) a gRNA targeting murine ITGB3 exon 3; iii) a gRNA targeting murine ITGB3 exon 10; iv) a single stranded homology directed repair (HDR) template oligonucleotide encoding T30A, S32P, Q33L, and N39D mutations in GPIIIa relative to SEQ ID NO:25; and ii) a single stranded HDR template oligonucleotide encoding a M470Q mutation in GPIIIa relative to SEQ ID NO:25; implanting two-cell stage embryos generated from the injected oocytes into oviducts of a pseudo-pregnant female mouse; and screening mice born from the pseudo-pregnant female for presence of the T30A, S32P, Q33L, N39D, and M470Q mutation in GPIIIa relative to SEQ ID NO:25. In some embodiments, the gRNA targeting ITGB3 exon 10 comprises SEQ ID NO:7. In some embodiments, the single stranded HDR template oligonucleotide encoding a M470Q mutation additionally encodes a diagnostic restriction site. In some embodiments, the single stranded HDR template oligonucleotide encoding a M470Q mutation additionally encodes one or more silent mutations to ITGB3 exon 10 to silence repetitive digestion by Cas9 of ITGB3 at exon 10. In some embodiments, the single stranded HDR template oligonucleotide encoding a M470Q mutation comprises SEQ ID NO:8. In some embodiments, the gRNA targeting ITGB3 exon 3 comprises SEQ ID NO: 1. In some embodiments, the single stranded HDR template oligonucleotide encoding T30A, S32P, Q33L, and N39D mutations additionally encodes a diagnostic restriction site. In some embodiments, the single stranded HDR template oligonucleotide encoding T30A, S32P, Q33L, and N39D mutations additionally encodes one or more silent mutations to ITGB3 exon 3 to silence repetitive digestion by Cas9 of ITGB3 at exon 3. In some embodiments, the single stranded HDR template oligonucleotide encoding T30A, S32P, Q33L, and N39D mutations comprises SEQ ID NO:4.

In a ninth aspect, provided herein is a transgenic mouse whose genome comprises a nucleic acid encoding a variant platelet membrane glycoprotein IIIc (GPIIIa) having at least 95% identity to SEQ ID NO: 27, wherein the variant GPIIIa comprises mutations T30A, S32P, Q33L, N39D, and M470Q relative to SEQ ID NO: 25. In some embodiments, the mouse expresses a variant GPIIIa comprising the sequence set forth in SEQ ID NO:27. In some embodiments, the variant GPIIIa can bind to an anti-HPA-1a antibody.

In a tenth aspect, provided herein is a mouse pregnant with pups heterozygous for wild-type platelet membrane glycoprotein IIIc (GPIIIa) and a variant GPIIIa comprising mutations T30A, S32P, Q33L, N39D, and M470Q relative to SEQ ID NO: 25. In some embodiments, the mouse is positive for anti-HPA-1a antibodies. In some embodiments, the mouse was immunized prior to pregnancy with (i) platelets from a transgenic mouse described herein or (ii) a variant GPIIIa comprising mutations T30A, S32P, Q33L, N39D, and M470Q relative to SEQ ID NO:25.

BRIEF DESCRIPTION OF DRAWINGS

The patent or patent application file contains at least one drawing in color. Copies of this patent or patent application publication with color drawings will be provided by the Office upon request and payment of the necessary fee.

FIGS. 2A-2F show CRISPR-mediated generation of the APLD humanized transgenic mouse. FIG. 2A: Three-dimensional structure of the GPIIIa PSI domain, showing the location of the residues that were mutated in the murine protein to humanize the 22-40 amino acid loop. FIG. 2B: Schematic illustration of the ITGB3 locus, showing the location of the gRNA binding site (red bar), the protospacer adjacent motif (PAM) sequence (magenta bar), and the Cas9 cleavage site (red arrow heads). A 200 bp APLD Homology Directed Repair (HDR) template was designed to introduce the four desired amino acid substitutions (mutated nucleotides labeled in red) and a diagnostic BamH1 restriction site (silent mutation nucleotides labeled in blue) flanked by 80 nucleotide homology arms. The HDR template also introduces nucleotides (green) that encode silent mutations to prevent re-cleavage by Cas9. FIG. 2C: The 20 bp gRNA shown in panel B, designed to target the Cas9 nuclease to the ITGB3 gene, was cloned into the BbsI site of the CRISPR vector px459, which also encodes both Cas9 and a puromycin-resistance gene. Pronuclei of C57BL/6N fertilized eggs were microinjected with the px459 plasmid along with the HDR template to generate the humanized APLD mouse. FIG. 2D: PCR strategy designed to report the incorporation of the HDR template within a 717 bp region surrounding the targeted site of the murine ITGB3 gene. The introduced BamH1 is marked by a blue box. FIG. 2E: Genotyping of two representative pups: Genomic DNA from the pups' tail was PCR amplified and digested with BamH1 to identify correctly targeted APLD alleles. The PCR product of Pup #1 cut with BamH1, demonstrating successful incorporation of the HDR oligo. The arrows indicate the expected BamH1 digestion products. FIG. 2F: The ITGB3 locus surrounding the genomic editing site was PCR-amplified from genomic DNA of Pup #1 and subjected to DNA sequence analysis, confirming precise homozygous integration of the human sequence into both alleles of murine ITGB3.

FIG. 3A: Flow cytometry analysis of the binding of the HPA-1a-selective murine mAb, SZ21 to human and mouse platelets. Note that SZ21 binds to human HPA-1a-, but not HPA-1b, -positive human platelets, demonstrating its allo-selectivity, and to APLD, but not wild-type, murine platelets. The PSI domain-specific mAb, PSIB1, was used as a positive control for expression of GPIIb-IIIa, and as shown, binds all PSI domains, regardless of species or HPA allotype. FIG. 3B: Antigen-capture ELISA analysis of anti-HPA-1a maternal alloantisera binding to human and murine forms of GPIIb-IIIa. Five different human FNAIT alloantisera were incubated with human or murine platelet of the indicated phenotype. Platelet/antibody complexes were then detergent lysed and added to microtiter wells that had been coated with either anti-mouse CD41 to capture immune complexes from mouse platelets, or mAb AP2 to capture immune complexes from human platelets. Note that human alloantisera 2, 3, and 4 react similarly with human GPIIb-IIIa and APLD murine GPIIb-IIIa, while alloantisera 1 and 5 do not react with murine APLD GPIIb-IIIa, suggesting that the preponderance of the HPA-1a-specific alloantibodies present in these polyclonal sera have more complex epitope requirements. None of the FNAIT alloantisera react with wild-type murine GPIIb-IIIa, as expected.

FIG. 4A: Flow cytometry analysis of the reactivity of HPA-1a-specific monoclonal antibodies with human and mouse platelets. Platelets from the indicated species, and having the indicated phenotypes, were reacted with mAbs SZ21, 26.4 and B2G1. Note that the Type II mAb 26.4 requires that murine GPIIIa be humanized from Met to Gln at residue 470 of the EGF1 domain, which is spatially close to the PSI domain, as depicted in FIG. 4B. Another Type II HPA-1a-specific mAb, B2G1, remains unreactive with APLDQ platelets, highlighting the complexity of binding specificities that are likely present in the polyclonal humoral response to the Leu33Pro polymorphism that controls formation of the HPA-1a epitope.

FIG. 5A: Comparison of human versus murine PSI and I-EGF1 domain sequences, with differences highlighted in red. Note especially the APLD sequences in the PSI domain and the Q470M, H446P, G463D, and P464Q differences within EGF1. FIG. 5B: Structural model of the variable region of antibody B2G1 bound with the β3 PSI and I-EGF1 domains. The antibody is shown as a tan surface with the CDR loops indicated, while the side chains of integrin β3 residues at the antigen-antibody interface are shown as sticks and dots. Note that interface interacting residues include not only polymorphic amino acid 33, but also $P_{32}$ in the PSI domain and $H_{446}$ and $Q_{470}$ of I-EGF1. Also note that $G_{463}$ and $P_{464}$ are nowhere near the interface. FIG. 5C top: HEK293 cells transiently transfected with plasmids expressing human GPIIb and a murine GPIIIa isoform that had been mutated to express the indicated humanized amino acid substitution were incubated with the indicated antibodies and subjected to flow cytometric analysis. The PSI domain-specific mAb, PSIB1, was used as a control for transfection efficiency. Note that mAb 26.4 requires $Q_{470}$ for its binding, while B2G1 requires both $Q_{470}$ and $H_{446}$, as predicted in the docking model in FIG. 5B. FIG. 5C bottom: HEK293 cells transfected with plasmids expressing human GPIIb and a human GPIIIa isoform that had been mutated to express the indicated mouse amino acids were subjected to flow cytometry analysis using the indicated antibodies. Note that the $Q_{470} \rightarrow M$ mutation results in loss of binding of both 26.4 and B2G1, while the $H_{446} \rightarrow P$ amino acid substitution affects only B2G1.

FIG. 6A: Three-dimensional structure of the GPIIIa PSI domain, showing the location of the residues M470 in EGF1 domains that was mutated to Q in the APLD murine GPIIIa protein. FIG. 6B: Schematic illustration of the ITGB3 locus, showing the location of the gRNA binding site (red bar), the protospacer adjacent motif (PAM) sequence (magenta bar) and the Cas9 cleavage site (red arrow heads). A 167 bp Homology Directed Repair (HDR) template was designed to introduce the M to Q amino acid substitutions (mutated nucleotides labeled in red) flanked by 82 and 77 nucleotides homology arms. The HDR template also introduces silent mutation (nucleotides in green) to prevent re-cleavage by Cas9. FIG. 6C: Cytoplasmic of APLD C57BL/6N fertilized eggs were microinjected with Cas-9 protein, gRNAs along with the HDR template to generate the humanized APLDQ mouse. FIG. 6D: The ITGB3 locus surrounding the genomic editing site was PCR-amplified from genomic DNA of Pup and subjected to DNA sequence analysis, confirming precise heterozygous integration of the HDR sequence into one allele of murine ITGB3.

INCORPORATION BY REFERENCE

Figures 1A, 1B:
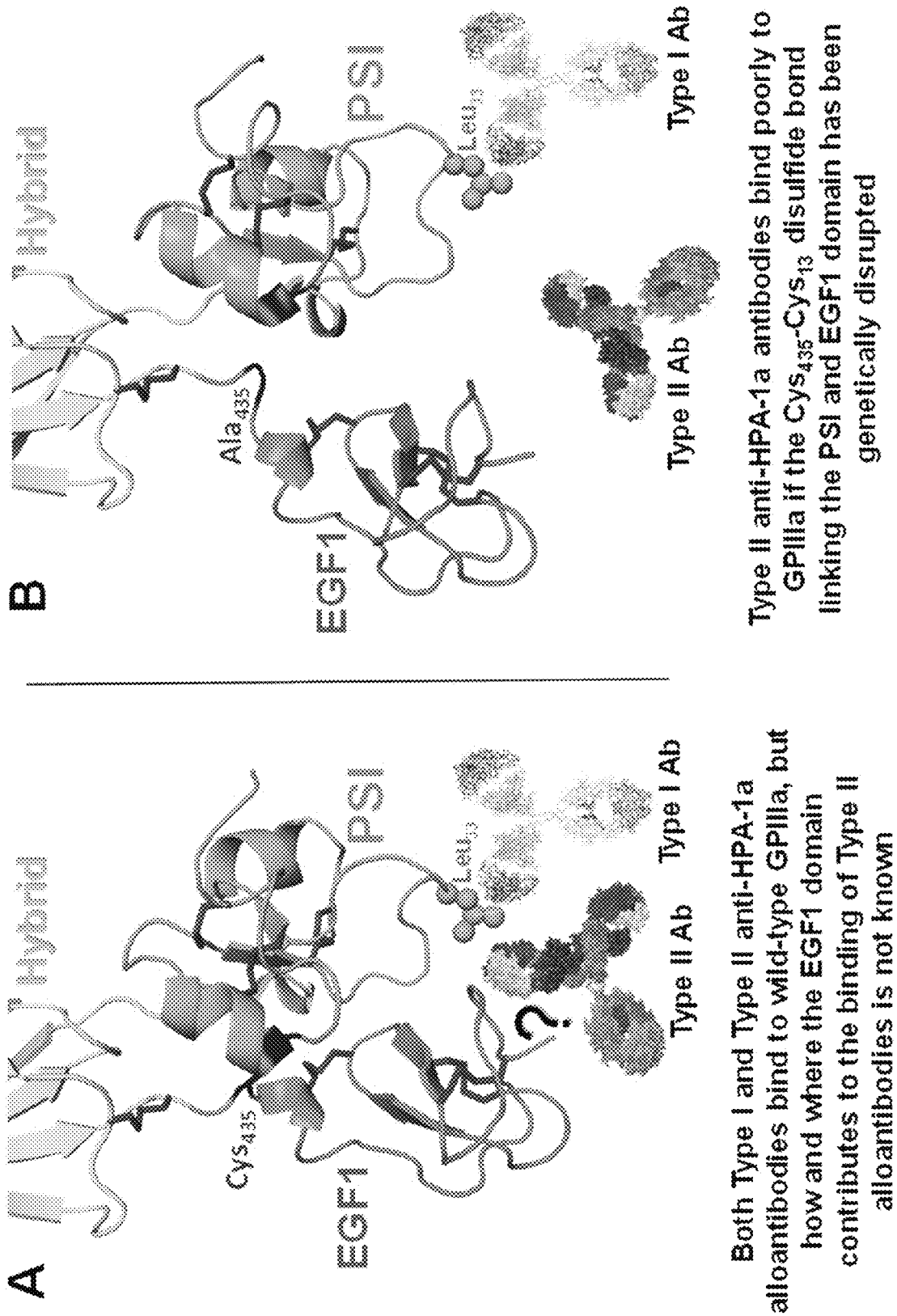
FIGS. 1A-1B shows the three-dimensional structure of the human GPIIIa PSI and EGF1 domains. Note that the PSI domain lies between the hybrid and EGF1 domains of GPIIIa, and that polymorphic amino acid 33, which controls expression of the HPA-1a ($PI^{A1}$) epitope, is directly opposite the linearly distant, but conformationally close, EGF1 domain. Mutation of alanine to $Cys_{435}$, which links the EGF1 domain to the PSI domain via a disulfide bond with $Cys_{13}$, has previously been shown to result in the loss of binding of some, but not all, maternal anti-HPA-1a alloantibodies, leading to speculation that non-polymorphic amino acids in EGF1 constitute part of the epitope for these so-called Type II antibodies.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE DISCLOSURE

FNAIT and PTP are bleeding disorders caused by alloantibodies to platelet-specific antigens. The HPA-1a (also known as Pl[A1]) epitope is the human platelet alloantigen that most commonly provokes PTP and FNAIT, being responsible for ~80% of the cases in which an alloantibody can be detected. The HPA-1a/-1b alloantigen system is controlled by a Leu33Pro polymorphism in platelet membrane glycoprotein (GP)IIIa[13,14] (=the β3 integrin subunit of the αIIbβ3 platelet fibrinogen receptor) with Pro33 (=HPA-1b) homozygous individuals who also carry the HLA-DRB3*0101 allele of the major histocompatibility complex (MHC) most at risk for developing an alloimmune response to the Leu33 (HPA-1a) form of GPIIIa[15-17]. Polymorphic amino acid 33 is located within a heavily disulfide-bonded knot-like structure known as the plexin, semaphorin, integrin (PSI) domain, which itself lies between the hybrid and integrin epidermal growth factor 1 (EGF, I-EGF1) domains of GPIIIa[18] (see FIGS. 1A-1B). Interestingly, while some maternal anti-HPA-1a alloantibodies, classified as Type I antibodies, bind normally to a mutant form of GPIIIa in which the disulfide bond linking the PSI and EGF1 domains together has been disrupted, others (Type II) lose reactivity[19], demonstrating (1) that the alloimmune response to HPA-1a is heterogeneous, and (2) that sequences within the linearly distant EGF domain might be required to form a high-affinity antibody binding site on GPIIIa for at least some maternal anti-HPA-1a antibodies (shown schematically in FIGS. 1A-1B).

Based on an analysis of the three-dimensional structure data of GPIIIa in the region of the molecule surrounding polymorphic amino acid 33, described herein are transgenic mice that expressed murine GPIIIa isoforms harboring select humanized residues within the PSI and EGF1 domain. Also described is binding of a series of monoclonal and polyclonal HPA-1a-specific antibodies to the GPIIIa isoforms harboring select humanized residues. The binding shows complex heterogeneity of the polyclonal alloimmune response to this clinically important human platelet alloantigen system. High-resolution mapping of this alloimmune response may improve diagnosis of FNAIT and should facilitate the rational design, selection, and/or screening for prophylactic and therapeutic anti-HPA-1a agents.

Currently, no animal model of FNAIT exists that accurately reflects the binding of a broad range of monoclonal and polyclonal antibodies from anti-HPA-1a antisera to GPIIIa as is seen in human FNAIT. Additionally, no animal model of FNAIT exists that is suitable for design, selection, and screening of prophylactic and therapeutic reagents. This is due to sequence and structural divergence of murine GPIIIa, compared to human GPIIIa, which results in altered binding monoclonal and polyclonal antibodies.

Provided herein is a transgenic mouse comprising humanizing mutations in GPIIIa. Because of the mutations in GPIIIa, the mouse expresses variant GPIIIa that binds monoclonal and polyclonal antibodies from anti-HPA-1a antisera. Also provided herein are cells and tissues derived from the transgenic mouse. The wild-type mouse GPIIIa sequence is included herein as SEQ ID NO:25. The transgenic mouse GPIIIa sequence comprises at least T30A, S32P, Q33L, N39D, and M470Q mutations in GPIIIa (SEQ ID NO:25), resulting in a variant GPIIIa capable of binding an anti-HPA-1a antibody, and, in some embodiments, monoclonal and polyclonal anti-HPA-1a antibodies. In some embodiments, the variant GPIIIa sequence comprises at least an M470Q mutation and a mutation of amino acid residues 22-40 of SEQ ID NO:25, wherein amino acid residues 22-40 are replaced with the sequence MCAWCSDEALPLGSPRCD (SEQ ID NO:28) which corresponds to the loop region in the PSI domain and adjacent to the EGF1 and EGF2 domains of human GPIIIa. In one embodiment, the variant GPIIIa is capable of binding the monoclonal antibody 26.4. In some embodiments, the transgenic mouse expresses a variant GPIIIa comprising the amino acid sequence of SEQ ID NO:26. In some embodiments, the transgenic mouse expresses a variant GPIIIa comprising the amino acid sequence of SEQ ID NO:27.

```
Murine GPIIIa
                                                      (SEQ ID NO: 25)
ESNICTTRGVNSCQQCLAVSPVCAWCSDETLSQGSPRCNLKENLLKDNCAPESIEFPVSE

AQILEARPLSSKGSGSSAQITQVSPQRIALRLRPDDSKIFSLQVRQVEDYPVDIYYLMDLS

FSMKDDLSSIQTLGTKLASQMRKLTSNLRIGFGAFVDKPVSPYMYISPPQAIKNPCYNMK

NACLPMFGYKHVLTLTDQVSRFNEEVKKQSVSRNRDAPEGGFDAIMQATVCDEKIGWR

NDASHLLVFTTDAKTHIALDGRLAGIVLPNDGHCHIGTDNHYSASTTMDYPSLGLMTEK

LSQKNINLIFAVTENVVSLYQNYSELIPGTTVGVLSDDSSNVLQLIVDAYGKIRSKVELEV

RDLPEELSLSFNATCLNNEVIPGLKSCVGLKIGDTVSFSIEAKVRGCPQEKEQSFTIKPVGF

KDSLTVQVTFDCDCACQAFAQPSSPRCNNGNGTFECGVCRCDQGWLGSMCECSEEDYR

PSQQEECSPKEGQPICSQRGECLCGQCVCHSSDFGKITGKYCECDDFSCVRYKGEMCSG

HGQCNCGDCVCDSDWTGYYCNCTTRTDTCMSTNGLLCSGRGNCECGSCVCVQPGSYG

DTCEKCPTCPDACSFKKECVECKKFNRGTLHEENTCSRYCRDDIEQVKELTDTGKNAVN

CTYKNEDDCVVRFQYYEDTSGRAVLYVVEEPECPKGPDILVVLLSVMGAILLIGLATLLI

WKLLITIHDRKEFAKFEEERARAKWDTANNPLYKEATSTFTNITYRGT

Humanized Murine GPIIIa variant 1
                                                      (SEQ ID NO: 26)
ESNICTTRGVNSCQQCLAVSPVCAWCSDEALPLGSPRCDLKENLLKDNCAPESIEFPVSE

AQILEARPLSSKGSGSSAQITQVSPQRIALRLRPDDSKIFSLQVRQVEDYPVDIYYLMDLS

FSMKDDLSSIQTLGTKLASQMRKLTSNLRIGFGAFVDKPVSPYMYISPPQAIKNPCYNMK

NACLPMEGYKHVLTLTDQVSRFNEEVKKQSVSRNRDAPEGGFDAIMQATVCDEKIGWR

NDASHLLVETTDAKTHIALDGRLAGIVLPNDGHCHIGTDNHYSASTTMDYPSLGLMTEK

LSQKNINLIFAVTENVVSLYQNYSELIPGTTVGVLSDDSSNVLQLIVDAYGKIRSKVELEV

RDLPEELSLSFNATCLNNEVIPGLKSCVGLKIGDTVSFSIEAKVRGCPQEKEQSFTIKPVGE

KDSLTVQVTFDCDCACQAFAQPSSPRCNNGNGTFECGVCRCDQGWLGSQCECSEEDYR

PSQQEECSPKEGQPICSQRGECLCGQCVCHSSDFGKITGKYCECDDFSCVRYKGEMCSG
```

```
-continued
HGQCNCGDCVCDSDWTGYYCNCTTRTDTCMSTNGLLCSGRGNCECGSCVCVQPGSYG

DTCEKCPTCPDACSFKKECVECKKFNRGTLHEENTCSRYCRDDIEQVKELTDTGKNAVN

CTYKNEDDCVVRFQYYEDTSGRAVLYVVEEPECPKGPDILVVLLSVMGAILLIGLATLLI

WKLLITIHDRKEFAKFEEERARAKWDTANNPLYKEATSTFTNITYRGT

Humanized Murine GPIIIa variant 2
                                                    (SEQ ID NO: 27)
ESNICTTRGVNSCQQCLAVSPMCAWCSDEALPLGSPRCDLKENLLKDNCAPESIEFPVS

EAQILEARPLSSKGSGSSAQITQVSPQRIALRLRPDDSKIFSLQVRQVEDYPVDIYYLMDL

SFSMKDDLSSIQTLGTKLASQMRKLTSNLRIGFGAFVDKPVSPYMYISPPQAIKNPCYNM

KNACLPMFGYKHVLTLTDQVSRFNEEVKKQSVSRNRDAPEGGFDAIMQATVCDEKIGW

RNDASHLLVFTTDAKTHIALDGRLAGIVLPNDGHCHIGTDNHYSASTTMDYPSLGLMTE

KLSQKNINLIFAVTENVVSLYQNYSELIPGTTVGVLSDDSSNVLQLIVDAYGKIRSKVELE

VRDLPEELSLSLFNATCLNNEVIPGLKSCVGLKIGDTVSFSIEAKVRGCPQEKEQSFTIKPV

GFKDSLTVQVTFDCDCACQAFAQPSSPRCNNGNGTFECGVCRCDDQGWLGSQCECSEED

YRPSQQEECSPKEGQPICSQRGECLCGQCVCHSSDFGKITGKYCECDDFSCVRYKGEMC

SGHGQCNCGDCVCDSDWTGYYCNCTTRTDTCMSTNGLLCSGRGNCECGSCVCVQPGS

YGDTCEKCPTCPDACSFKKECVECKKFNRGTLHEENTCSRYCRDDIEQVKELTDTGKNA

VNCTYKNEDDCVVRFQYYEDTSGRAVLYVVEEPECPKGPDILVVLLSVMGAILLIGLAT

LLIWKLLITIHDRKEFAKFEEERARAKWDTANNPLYKEATSFTNITYRGT
```

As used herein, the term "variant" refers to a polypeptide having one or more amino acid substitutions, deletions, and/or insertions compared to a reference sequence. For example, SEQ ID NO: 26 is a variant of SEQ ID NO: 25. The variant GPIIIa can have, for example, an amino acid sequence that is at least 80%, at least 85%, at least 90%, at least 95%, at least 96%, at least 97%, at least 98%, or at least 99% identical to SEQ ID NO:25 and that comprises T30A, S32P, Q33L, N39D, and M470Q mutations relative to SEQ ID NO:25. In some embodiments, the variant GPIIIa comprises T30A, S32P, Q33L, N39D, and M470Q mutations relative to SEQ ID NO:25 and 1, 2, 3, 4, 5, 6, 7, 8, 9, 10, up to 15, up to 20, up to 25, or up to 30 additional amino acid substitutions relative to SEQ ID NO:25. In some embodiments, the amino acid substitutions are conservative substitutions.

The term "conservative substitution" as used herein denotes that one or more amino acids are replaced by another, biologically similar residue. Examples include substitution of amino acid residues with similar charactetistics, e.g, small amino acids, acidic amino acids, polar amino acids, basic amino acids, hydrophobic amino acids, and aromatic amino acids. For further information concerning phenotypically silent substitutions in peptides and proteins, see, for example, Bowie et. al., Science 247:1306-1310 (1990). In the table below, conservative substitutions of amino acids are grouped by physicochemical properties; I: neutral and/or hydrophilic, II: acids and amides, III: basic, IV: hydrophobic, V: aromatic, bulky amino acids.

TABLE I

| I | II | III | IV | V |
|---|----|-----|----|---|
| A | N  | H   | M  | F |
| S | D  | R   | L  | Y |
| T | E  | K   | I  | W |
| P | Q  |     | V  |   |
| G |    |     | C  |   |

In the table below, conservative substitutions of amino acids are grouped by physicochemical properties; VI: neutral or hydrophobic, VII: acidic, VIII: basic, IX: polar, X: aromatic.

TABLE II

| VI | VII | VIII | IX | X |
|----|-----|------|----|---|
| A  | D   | H    | M  | F |
| L  | E   | R    | S  | Y |
| I  |     | K    | T  | W |
| V  |     |      | N  | H |
| P  |     |      | Q  |   |
| G  |     |      | C  |   |

Methods of identifying conservative nucleotide and amino acid substitutions which do not affect protein function are well-known in the art (see, e.g., Brummell et al., Biochem. 32:1180-1187 (1993); Kobayashi et al., Protein Eng. 12(10):879-884 (1999); and Burks et al., Proc. Natl. Acad. Sci. USA 94:412-417 (1997)).

The terms "identical" or percent "identity" in the context of two or more nucleic acids or polypeptides, refers to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms, or by visual inspection. Various algorithms and software are known in the art that can be used to obtain alignments of amino acid or nucleotide sequences.

One such non-limiting example of a sequence alignment algorithm is described in Karlin et al., *Proc. Natl. Acad. Sci.*, 87:2264-2268 (1990), as modified in Karlin et al., *Proc. Natl Acad. Sci.*, 90:5873-5877 (1993), and incorporated into the NBLAST and. XBLAST programs (Altschul et al., *Nucleic Acids Res.*, 25:3389-3402 (1991)). In certain embodiments, Gapped BLAST can be used as described in Altschul et al., Nucleic Acids Res. 25:3389-3402 (1997). BLAST-2, WU-BLAST-2 (Altschul et al., *Methods in Enzymology,* 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used. Other resources for calculating identity include methods described in *Computational Molecular Biology* (Lesk ed., 1988); *Biocomputing: Informatics and Genome Projects* (Smith ed., 1993); *Computer Analysis of Sequence Data, Part* 1 (Griffin and Griffin eds., 1994); *Sequence Analysis in Molecular Biology* (G. von Heinje, 1987); *Sequence Analysis Primer* (Gribskov et al. eds., 1991); and Carillo et al., *SIAM J. Applied Math.*, 48:1073 (1988).

As used herein, "transgenic animal" refers to a non-human animal, such as a mammal, generally a rodent such as a rat or mouse, in which one or more (preferably all) of the cells of the animal includes a transgene as described herein. Other examples of transgenic animals include non-human primates, sheep, dogs, cows, goats, chickens, amphibians, and the like. As used herein, "transgene" refers to exogenous DNA that is integrated into the genome of a cell from which a transgenic animal develops and thus remains in the genome of the mature animal, thereby directing the expression of an encoded gene product in one or more cell types or tissues of the transgenic animal. Knock-out animals are included in the definition of transgenic animals.

Methods for generating transgenic animals, particularly animals such as mice, via embryo manipulation and electroporation or microinjection of pluripotent stem cells or oocytes, are known in the art and are described, for example, in U.S. Pat. Nos. 4,736,866 and 4,870,009, 4,873,191, U.S. Ser. No. 10/006,611, "Transgenic Mouse Methods and Protocols (Methods in Molecular Biology)," Hofker and van Deursen, Editors (Humana Press, Totowa, N.J., 2002); and in "Manipulating the Mouse Embryo," Nagy et al., Editors (Cold Spring Harbor Laboratory Press, Cold Spring Harbor, N.Y., 2002), which are incorporated herein by reference in their entirety.

In general, a transgenic mouse as described herein is made by injecting a vector made as described herein into the pronuclei or cytoplasm of a fertilized mouse oocyte and used for generation of a transgenic mouse with T30A, S32P, Q33L, N39D, and M470Q mutations, relative to SEQ ID NO:25, in GPIIIa in all cells, using standard transgenic techniques, e.g., as described in "Transgenic Mouse Methods and Protocols (Methods in Molecular Biology)," Hofker and van Deursen, Editors (Humana Press, Totowa, N.J., 2002); U.S. Pat. Nos. 4,736,866 and 4,870,009, 4,873,191 and 6,791,006, and in Hogan, "Manipulating the Mouse Embryo," Nagy et al., Editors (Cold Spring Harbor Laboratory Press, Cold Spring Harbor, N.Y., 2002).

Methods for mutating genes are known in the art. See, for example, U.S. Pat. No. 7,022,893 to Takeda et al. and U.S. Pat. No. 6,218,595 to Giros et al., as well as U.S. Pat. No. 6,344,596 to W. Velander et al. (American Grey Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Grey Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to J. M. Hyttinin et al. (Pharming BV); U.S. Pat. No. 5,880,327 to H. Lubon et al. (American Grey Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Grey Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

In some embodiments, the transgenic mouse as described herein is generated using CRISPR/Cas9 mediated homology directed repair (HDR). See, for example, Wang et al. ("One-step generation of mice carrying mutations in multiple genes by CRISPR/Cas-mediated genome editing," Cell, 2013, 153(4):910-918). To mutate GPIIIa and create the transgenic mouse, a vector, encoding both i) the Cas9 nuclease and ii) guide RNA (gRNA) targeting the region of interest and preceding a protospacer adjacent motif (PAM) site, and a single stranded oligodeoxynucleotide (ssODN) homology directed repair template are injected into the pronuclei or cytoplasm of fertilized murine oocytes. In some embodiments, isolated gRNA, ssODN HDR template, and Cas9 nuclease are injected into the pronuclei or cytoplasm of fertilized murine oocytes. In some embodiments, the vector comprises a reporter gene or selectable markers.

In some embodiments, the gRNA targets murine ITGB3 exon 3 and the ssODN HDR template encodes the GPIIIa T30A, S32P, Q33L, and N39D mutations. In some embodiments, the gRNA that targets murine ITGB3 exon 3 has the sequence 5'-TTCTCCTTCAGGTTACATCG-3' (SEQ ID NO:1). In some embodiments, the ssODN HDR template encoding GPIIIa T30A, S32P, Q33L, and N39D mutations has the sequence 5'-GCCAGGGGGAGGTGACT-TACCAGGCAGGAGGCACAGCCGCCCTAGCTCT-GATGTTG ACCTTTCCCTCGGGCTCTTCTCTTCAT-AGGCCTTGCCTCTGGGATCCCCACGCTGTGA CCTGAAGGAGAACCTGCTGAAGGACAAT-TGTGCTCCAGAGTCTATTGAGTTCCCAGT CAGT-GAGGCCCAGATCCTGGAGGCTAGGC-3' (SEQ ID NO:4). In some embodiments, the ssODN HDR template encodes silent mutations introducing a diagnostic restriction site. In some embodiments, the ssODN HDR template encodes silent mutations to the target gene of interest to silence repetitive digestion of the resulting mutated gene by Cas9.

Figures 6A, 6B, 6C, 6D:
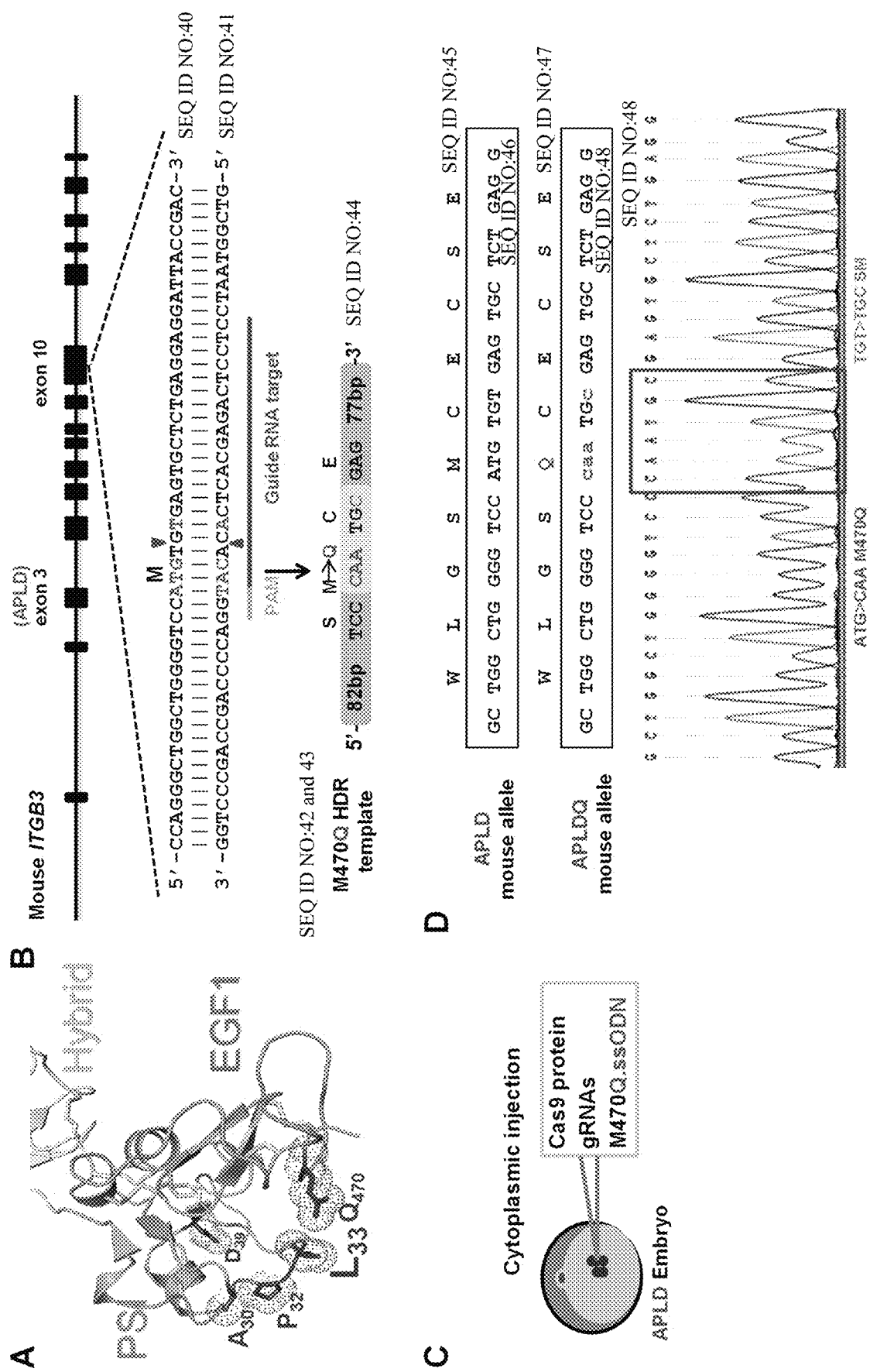
FIGS. 6A-6D show CRISPR-mediated generation of the APLDQ humanized transgenic mouse.

The murine ITGB3 gene sequence is available as NCBI Gene ID:16416 and GenBank NC_000077.6. The genomic, nucleotide mutations that correspond to the A30, P32, L33, D39, and Q470 mutations in ITGB3 are outlined in FIG. 2B and FIG. 6B.

In some embodiments, the gRNA targets ITGB3 exon 10 and the ssODN HDR template encodes the GPIIIa M470Q mutation. In some embodiments, the gRNA that targets murine ITGB3 exon 10 has the sequence 5'-CTCCTCAGAGCACTCACACA-3' (SEQ ID NO:7). In some embodiments, the ssODN HDR template encoding the GPIIIa M470Q mutation has the sequence 5'-AGCCTTCCAGCCCACGCTGCAACAATGG-GAACGGGACTTTTGAGTGTGGGGTGTGCC GCTGTGACCAGGGCTGGCTGGGGTCC-CAATGCGAGTGCTCTGAGGAGGATTACCGA CCCTCTCAGCAGGAAGAGTGCAGCCC-CAAGGAGGGCCAGCCCATCTGCAGCCA-3' (SEQ ID NO:8). In some embodiments, the ssODN HDR template encodes silent mutations introducing a diagnostic restriction site. In some embodiments, the ssODN HDR template encodes silent mutations to the target gene of interest to silence repetitive digestion of the resulting mutated gene by Cas9.

A transgenic founder animal can be identified based upon the presence of T30A, S32P, Q33L, N39D, and M470Q mutations in GPIIIa. The presence of the mutations may be detected directly, for example, by PCR amplification or sequencing of the region of interest of the GPIIIa gene. A transgenic founder animal can then be used to breed additional animals carrying the transgene. Additionally, the transgenic animal carrying the T30A, S32P, Q33L, N39D, and M470Q mutations in GPIIIa can further be bred with other transgenic animals carrying other transgenes.

The transgenic animals described herein, as well as cells and tissues derived therefrom, are useful in the identification and study of factors that can bind to variant GPIIIa, for example, monoclonal or polyclonal anti-HPA-1a antibodies or fragments thereof. In some embodiments, the transgenic animal described herein may be used to characterize test factors useful in the treatment or prevention of RPT, PTP, or FNAIT, for example, by monitoring platelet count, platelet concentration, bleeding, or pharmacokinetics of the test factors.

Methods of Screening

The invention provides in vitro and in vivo screening methods. One embodiment is an in vitro method of identifying a molecule that is able to specifically bind to a variant glycoprotein IIIa (GPIIIa). In one aspect of this embodiment, a candidate molecule is contacted with platelets from a transgenic mouse whose genome comprises a nucleic acid encoding a variant GPIIIa, wherein the variant GPIIIa comprises mutations T30A, S32P, Q33L, N39D, and M470Q relative to SEQ ID NO:25. If the candidate molecule binds to platelets from the transgenic mouse, but does not bind to platelets from a wild-type mouse or a mouse not comprising the variant GPIIIa, then the candidate molecule can be considered to bind specifically to the variant GPIIIa.

Platelet binding can be measured qualitatively or quantitatively by known methods, including flow cytometry, immunohistochemistry, radioimmunoassay, ELISA, fluorescence resonance energy transfer (FRET), biolayer interferometry, and surface plasmon resonance.

Another in vitro method can identify a molecule that is able to compete with an anti-HPA-1a antibody for binding to a variant GPIIIa of the invention. In one embodiment, the method comprises (a) contacting the variant GPIIIa with the anti-HPA-1a antibody to form a GPIIIa-antibody complex, wherein the variant GPIIIa is immobilized on a substrate and wherein the anti-HPA-1a antibody comprises a label; (b) contacting the GPIIIa-antibody complex with a candidate molecule in solution; and (c) determining whether the candidate molecule competes for anti-HPA-1a antibody binding to the variant GPIIIa by detecting the amount of label on the substrate or in the solution. The candidate molecule competes with the antibody by binding to the variant GPIIIa and preventing binding of the antibody. A positive result in this assay indicates that the binding site of the candidate molecule to GPIIIa overlaps with or comprises the epitope on GPIIIa to which the antibody binds. In a particular embodiment, the variant GPIIIa comprises the amino acid sequence set forth in SEQ ID NO: 26.

A "label" is a detectable compound that can be conjugated directly or indirectly to a molecule, so as to generate a labeled molecule. The label can be detectable on its own (e.g., radioisotope labels or fluorescent labels), or can be indirectly detected, for example, by catalyzing chemical alteration of a substrate compound or composition that is detectable (e.g., an enzymatic label) or by other means of indirect detection (e.g., biotinylation). In one embodiment, the label is selected from the group consisting of a fluorophore, a radioisotope, a chemiluminescent probe, and a bioluminescent probe.

Prevention of anti-HPA-1a antibody binding by the candidate molecule (i.e., competition) can be determined by detecting the presence or absence of the label. For example, if the method is performed via chromatography, presence of the label in the eluate indicates competition by the candidate molecule for binding to the variant GPIIIa; absence of the label indicates retention/binding of the antibody on the immobilized GPIIIa (i.e., no or limited competition). Alternatively, the substrate on which the antibody is immobilized can be analyzed for presence or absence of the label, wherein presence of the label indicates limited or no competition by the candidate molecule, and absence of the label indicates that the candidate molecule has bound to GPIIIa and prevented binding of the antibody (i.e., competes). I In certain embodiments, the HPA-1a antibody is a monoclonal antibody selected from the group consisting of PSIB1, SZ21, and 26.4. In a particular embodiment, the anti-HPA-1a antibody is 26.4.

The variant GPIIIa can be immobilized on any porous or non-porous substrate known in the art. Non-limiting examples of immobilization substrates include beads, resins, particles, membranes, and gels. Substrates can be comprised of a variety of materials, including agarose, alginate, glass, and magnetic materials. Immobilization can be achieved using any known method, such as adsorption, affinity tag binding, or covalent bonding.

Among in vivo methods provided by the invention is a method of identifying a molecule that is able to prevent an anti-HPA-1a alloimmune response in a female mouse. In one embodiment, the method comprises administering to a test mouse a candidate molecule, wherein the test mouse is pregnant with pups heterozygous for wild-type platelet membrane glycoprotein IIIc (GPIIIa) and a variant GPIIIa comprising mutations T30A, S32P, Q33L, N39D, and M470Q relative to SEQ ID NO:25, and wherein the test mouse is negative for anti-HPA-1a antibodies; and measuring anti-HPA-1a antibody titer in the test mouse. The candidate molecule is able to prevent an anti-HPA-1a alloimmune response if the anti-HPA-1a antibody titer in the test mouse is undetectable at delivery, at one week, two weeks, three weeks, four weeks, five weeks, six weeks, seven weeks, eight weeks, nine weeks, and/or ten weeks postpartum.

The invention further provides an in vivo method of identifying a molecule that is able to inhibit an anti-HPA-1a alloantibody from crossing the placenta of a pregnant mouse. In one embodiment, the method comprises administering to a test mouse a candidate molecule, wherein the test mouse pregnant with pups heterozygous for wild-type platelet membrane glycoprotein IIIa (GPIIIa) and a variant GPIIIa comprising mutations T30A, S32P, Q33L, N29D, and M470Q relative to SEQ ID NO:25, and wherein the test mouse was immunized prior to pregnancy with (i) platelets from the transgenic mouse of claim 1 or (ii) a variant GPIIIa comprising mutations T30A, S32P, Q33L, N29D, and M470Q relative to SEQ ID NO:25; and measuring fetal or neonatal anti-HPA-1a antibody titer. The candidate molecule is able to inhibit an anti-HPA-1a alloantibody from crossing the placenta of the pregnant mouse if the fetal or neonatal antibody titer in pups of the test mouse is lower than the fetal or neonatal antibody titer in pups of a control mouse.

Also provided is an in vivo method of identifying a molecule that is able to inhibit an anti-HPA-1a alloantibody from binding to fetal or neonatal platelets. In one embodiment, the method comprises administering to a test mouse a candidate molecule, wherein the test mouse pregnant with pups heterozygous for wild-type platelet membrane glycoprotein IIIa (GPIIIa) and a variant GPIIIa comprising mutations T30A, S32P, Q33L, N29D, and M470Q relative to SEQ ID NO:25, and wherein the test mouse was immunized prior to pregnancy with (i) platelets from the transgenic mouse of claim 1 or (ii) a variant GPIIIa comprising mutations T30A, S32P, Q33L, N29D, and M470Q relative to SEQ ID NO:25; and measuring fetal or neonatal platelet count. The candidate molecule is able to inhibit an anti-HPA-1a alloantibody from binding to fetal or neonatal platelets if the fetal or neonatal platelet count in pups of the test mouse is higher than the fetal or neonatal platelet count in pups of a control mouse.

As used herein, a "control mouse" is one that comprises the same conditions and is assessed in the same manner and in the same timeframe as the test mouse to which it is being compared, except that the control mouse has not been treated with the candidate molecule. For example, where the test mouse was immunized with platelets from a transgenic mouse of the invention or with a variant GPIIIa of the invention prior to pregnancy, the control mouse was pre-immunized under the same conditions. Likewise, in methods of the invention where the test mouse, is pregnant with pups heterozygous for wild-type GPIIIa and a variant GPIIIa comprising mutations T30A, S32P, Q33L, N39D, and M470Q relative to SEQ ID NO:25, the control mouse is pregnant with heterozygous pups as well. Where certain parameters are measured and/or outcomes are compared between a test mouse and a control mouse, the measurement or assessment is made using the same techniques/assays, under the same conditions. To achieve pregnancy with heterozygous pups, a wild-type female mouse is bred with a transgenic male mouse of the invention.

A wide variety of candidate molecules can be screened according to the methods of the invention. As used herein, a "candidate molecule" can be any chemical compound. Macromolecules, such as peptides, polypeptides, protein complexes, glycoproteins, antibodies, oligonucleotides, and nucleic acids, and small molecules, such as amino acids, nucleotides, organic compounds, inorganic compounds and organometallic compounds, are examples of candidate compounds. The candidate molecule can be naturally occurring, synthetic, or can include both natural and synthetic components.

Antibodies for use or screening in methods of the invention can include human antibodies, humanized antibodies, chimeric antibodies, monoclonal antibodies, polyclonal antibodies, recombinant antibodies, bispecific antibodies, multispecific antibodies, and antigen-binding fragments thereof. Antigen-binding fragments include Fv, F(ab), F(ab'), and F(ab')$_2$. Single-chain forms of each of the foregoing antibodies and antigen-binding fragments are also included.

In some embodiments, the candidate molecule can be a member of a library, e.g., an inorganic or organic chemical library, a peptide library, an oligonucleotide library, an antibody library, or mixed-molecule library. In some embodiments, the methods include screening small molecules, e.g., natural products or members of a combinatorial chemistry library.

In the instance where the candidate molecule is part of a library, for example, a library comprising antibodies or antigen-binding fragments thereof, the variant GPIIIa of the invention can be used in an epitope binning assay. Epitope binning is a competitive immunoassay that can be used to characterize and sort a library of monoclonal antibodies against a target antigen, for example, a protein comprising the amino acid sequence set forth in SEQ ID NO: 26. Antibodies against a similar target are tested against all other antibodies in the library in a pairwise fashion to determine whether antibodies block one another's binding to the epitope of an antigen. A competitive blocking profile for each antibody is created against all of the other antibodies in the library. Closely related binning profiles indicate that the antibodies have the same or a closely related epitope and are "binned" together. (See, e.g., Brooks B. D., Curr. Drug Discovery Technol. 11:109-112 (2014); Estep P. et at., MAbs 5:270-278 (2013).) Epitope binning is also referred to in the art as epitope mapping or epitope characterization.

Candidate molecules can be administered by methods known in the art, for example, by any of the oral, parenteral, inhalation, or topical routes. Parenteral administration includes, for example, intravenous, intraarterial, intraperitoneal, intramuscular, subcutaneous, rectal, and vaginal administration. Oral dosage forms include, for example, solid, liquid, and suspension formulations. Oral gavage is a preferred form of oral administration. Nasal aerosol or inhalation dosage forms can be prepared, for example, as solutions in saline, employing benzyl alcohol or other suitable preservatives, absorption promoters to enhance bioavailability, and/or other conventional solubilizing or dispersing agents. The candidate molecule can be administered in a composition comprising a buffer (e.g. acetate, phosphate or citrate buffer), optionally a surfactant (e.g. polysorbate), optionally a stabilizer agent (e.g. human albumin), etc. The form and character of the carrier or diluent can be dictated by the amount of active ingredient with which it is to be combined, the route of administration and other well-known variables. One of skill in the art can readily determine the appropriate route and dosage form, depending upon the structure and nature of the candidate molecule. Dosage of the candidate molecule can be determined empirically by the skilled artisan.

Depending on the method of the invention, the candidate molecule can be administered one time or multiple times at time points before pregnancy, during pregnancy, and post-partum. For example, the candidate molecule can be administered at one or more times between 1 and 14 days prior to mating, between days 1 and 24 post-mating, and/or between 1 and 28 days postpartum. In one embodiment, the candidate molecule is administered at day 10 and day 17 post-mating. One of ordinary skill can determine the dosing schedule empirically, depending upon the candidate molecule and the particular effect for which it is being screened.

In some methods of the invention, female mice are immunized with a variant GPIIIa prior to pregnancy to induce production of anti-HPA-1a antibodies. In some embodiments, immunization comprises administration of platelets from a transgenic mouse expressing a variant GPIIIa comprising mutations T30A, S32P, Q33L, N39D, and M470Q relative to SEQ ID NO:25. In some embodiments, immunization comprises administration of a variant GPIIIa, for example, comprising mutations T30A, S32P, Q33L, N39D, and M470Q relative to SEQ ID NO:25. Administration is via known methods, preferably by injection. Immunization can be performed, for example, at one or more times between 1 and 14 days prior to mating, during the gestational period of the mouse or following birth of the pup. In some embodiments, pre-immunization is performed at one or more times between 1 and 14 days prior to mating.

In certain methods of the invention, maternal, fetal, and/or neonatal anti-HPA-1a antibody titers are measured. Antibody titers can be measured in samples from an adult mouse, a neonatal mouse, or a fetal mouse. Antibody titers can be measured by known methods, including chemiluminescent microparticle immunoassay (CMIA), enzyme immunoassay (EIA), radioimmunoassay (MA), fluorescence activated cell sorting (FACS), lateral flow assay, enzyme linked immunosorbent assay (ELISA), and the like. For instance, antibody titer can be measured by coating the appropriate antigen, for example, HPA-1a, comprising a label onto a surface, such as beads, a microwell plate or microparticles, reacting the antigen with a sample to be analyzed, and then measuring the intensity of the label. Indirect immunoassays can also be used. In one embodiment, antibody titers are measured using a single-antigen bead assay. In one embodiment, antibody titers are expressed as mean fluorescence intensity (MFI) values.

Antibody titers can be assessed at one or more time points, depending on the screening assay. For example, antibody titers can be measured in a female mouse between 1 and 14 days prior to mating, between days 1 and 24 post-mating, and/or between 1 and 28 days postpartum. Antibody titers in a neonatal pup can be measured, for example, immediately after delivery, at 1, 2, 3, 4, 5, 6, 7, 8, 9, 10, 11, or 12 hours after delivery, and/or at 1, 2, 3, 4, 5, and/or 6 days after delivery, and/or at 1, 2, 3, and/or 4 days after delivery. Antibody titers in fetal pups can be measured, for example, at gestation day 10, 11, 12, 13, 14, 15, 16, 17, 18, 19, 20, 21, and/or 22. In some embodiments, antibody titers are measured in adult, neonatal, or fetal mice at 1, 2, 3, 4, 5, 6, 7, 8, 9, 10, 11, 12, 14, 16, 18, 20, 24, 30, 36, 42 and/or 48 hours, and/or at 1, 2, 3, 4, 5, and/or 6 days, and/or at 1, 2, 3, or 4 weeks after administration of a candidate molecule to the mother.

In some methods of the invention, fetal or neonatal platelet counts are measured in blood collected from dissected fetuses or from neonates. Platelet counts can be calculated manually using a hemocytometer, or can be measured by automated methods using, for example, optical light scatter/fluorescence analysis, flow cytometry, or impendence analysis. Platelet counts can be determined at one or more time points, depending on the screening assay. For example, platelet counts in a neonatal pup can be measured immediately after delivery, at 1, 2, 3, 4, 5, 6, 7, 8, 9, 10, 11, or 12 hours after delivery, and/or at 1, 2, 3, 4, 5, and/or 6 days after delivery, and/or at 1, 2, 3, and/or 4 days after delivery. Platelet counts in fetal pups can be measured, for example, at gestation day 10, 11, 12, 13, 14, 15, 16, 17, 18, 19, 20, 21, and/or 22. In some embodiments, platelet counts are measured in fetal or neonatal pups at 1, 2, 3, 4, 5, 6, 7, 8, 9, 10, 11, 12, 14, 16, 18, 20, 24, 30, 36, 42 and/or 48 hours, and/or at 1, 2, 3, 4, 5, and/or 6 days, and/or at 1, 2, 3, or 4 weeks after administration of a candidate molecule to the mother.

Bleeding is evaluated in fetal or neonatal pups in some aspects of the invention. "Bleeding" as used herein means an accumulation of blood in the body cavity, extremities, or cranium of the fetal or neonatal pup. In one embodiment, bleeding is intracranial bleeding. Bleeding can be assessed visually in dissected fetuses or in neonates.

One of skill in the art can determine the evaluation schedule, such as measurement of antibody titers, platelet counts, bleeding, and so forth, can be determined empirically, depending upon the candidate molecule and the particular effect for which it is being screened.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

Wherever embodiments are described with the language "comprising," otherwise analogous embodiments described in terms of "consisting of" and/or "consisting essentially of" are included.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value).

Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

The present invention has been described in terms of one or more preferred embodiments, and it should be appreciated that many equivalents, alternatives, variations, and modifications, aside from those expressly stated, are possible and within the scope of the invention.

EXAMPLES

Example 1

The embodiment described here demonstrates the generation of a murine model of FNAIT using CRISPR/Cas9-mediated homology directed repair. Specifically, this embodiment demonstrates generation of a transgenic mouse comprising T30A, S32P, Q33L, N39D, and M470Q mutations in GPIIIa, relative to SEQ ID NO:25.

Materials and Methods

Antibodies—Three antibodies with specificity for the Leu33 allelic isoform of human GPIIIa were used in this study: the murine monoclonal antibody (mAb) SZ21[20], the human mAb 26.4[21], derived from an immortalized B cell from an HPA-1a alloimmunized woman who had an infant affected by FNAIT, and B2G1[22]—a humanized IgG derived from an scFv fragment isolated by phage display from an HPA-1a alloimmunized woman. Human maternal anti-HPA-1a antisera were provided by Drs. Richard Aster, Dan Bougie, and Brian Curtis (Blood Research Institute, BloodCenter of Wisconsin, Milwaukee, Wis.). A murine mAb, PSIB1, which binds both the human and mouse β3 integrin PSI domain, and whose binding is unaffected by the Leu33Pro polymorphism[23], was kindly provided by Dr. Heyu Ni (University of Toronto). mAb AP2, which recognized a complex-dependent epitope on GPIIb-IIIa, but does not interfere with HPA-1a antibody binding[24], was provided by Dr. Robert Montgomery (Blood Research Institute, BloodCenter of Wisconsin).

One-step generation of mice expressing the APLD humanized form of murine GPIIIa—gRNAs were designed using the CRISPR Design Tool (crispr.mit.edu) to minimize off-target effects and selected to precede a 5'-NGG protospacer-adjacent motif (PAM). To generate the vector co-expressing Cas9 and sgRNA targeting ITGB3 Exon 3 (TTCTCCTTCAGGTTACATCG, SEQ ID NO:1), a pair of oligos (5'-CACCGTTCTCCTTCAGGTTACATCG-3' (SEQ ID NO:2) and 5'-AAACCGATGTAACCT-GAAGGAGAAC-3' (SEQ ID NO:3)) were annealed and cloned into the BbsI site of the Cas9 expression plasmid px459 (Addgene, Cambridge, Mass.). A single-stranded oligodeoxynucleotide (ssODN), 200 nucleotides in length, having the sequence 5'-GCCAGGGGGAGGTGACT-TACCAGGCAGGAGGCACAGCCGCCCTAGCTCTG-ATGTTGACCTTTCCCTCGGGCTCTTCTTCAT-AGGCCTTGCCTCTGGGATCCCCACG CTGTGACCTGAAGGAGAACCTGCTGAAGGACAAT-TGTGCTCCAGAGTCTATTGAGTT CCCAGTCAGT-GAGGCCCAGATCCTGGAGGCTAGGC-3' (SEQ ID NO:4) was synthesized by Integrated DNA Technologies (IDT, Coralville, Iowa). This oligo corresponds to the antisense strand of the murine β3 gene, and contains five nucleotide substitutions that result in the introduction of four human amino acid substitutions into the PSI domain of the murine β3 integrin subunit. The ssODN also contains four silent mutations, two of which introduce a diagnostic BamH1 restriction site into the plasmid, and two of which mutates the sequence to avoid repetitive digestion of the humanized murine β3 gene by Cas9.

C57BL/6N female mice were superovulated and mated with C57BL/6N males, and fertilized eggs were collected from the oviduct. The px459 plasmid (10 ng/μl) and ssODN (5 ng/μl) were injected into the pronuclei of fertilized oocytes. Injected zygotes were cultured in potassium simplex optimization medium (KSOM) with amino acids at 37° C. in 5% CO$_2$ and 95% humidified air overnight. Two-cell stage embryos were then transferred into the oviducts of pseudo-pregnant female mice. Genomic DNA isolated from the tail of the pups was genotyped by PCR and subsequent sequence analysis. The region surrounding the targeted locus was amplified using GPIIIa fw1: 5'-AACCATG-GAAGGACCATGAC-3' (SEQ ID NO:5) and GPIIIa rev1: 5'-CACCCCAGTCCTATCCTG-TG-3' (SEQ ID NO:6). PCR reactions were carried out using Herculase II Fusion polymerase (Agilent, Waldbronn, Germany). PCR products were purified using QiaQuick Spin Column, digested with BamH1 (New England Biolabs Inc., Ipswich, Mass.) analyzed on 2% agarose gels, and sequenced to confirm that the DNA double strand break had been faithfully repaired.

One-step generation of mice expressing the APLDQ humanized form of murine GPIIIa The CRISPR/Cas9 microinjection cocktail, including gRNA (CTCCTCAGAGCACTCACACA, (SEQ ID NO:7)), ssODN 5'-AGCCTTCCAGCC-CACGCTGCAACAATGGGAACGGGACTTTT-GAGTGTGGGGTGTGCC GCTGTGACCAGGGCTGGCTGGGGTCC-CAATGCGAGTGCTCTGAGGAGGATTACCGA CCCTCTCAGCAGGAAGAGTGCAGCCC-CAAGGAGGGCCAGCCCATCTGCAGCCA-3' (SEQ ID NO:8) and Cas-9 protein were injected into the cytoplasm of fertilized APLD GPIIIa oocytes (FIGS. 6A-6D). Mice born from the microinjection were screened for the presence of the desired point mutation by PCR and subsequent sequencing analysis. The region surrounding the targeted locus was amplified using GPIIIa fw2: 5'-GAGAAGGAGCAGTCTTT-CACTATCAAGCC-3' (SEQ ID NO:9) and GPIIIa rev2: 5'-GCAGGAGAAGTCATCGCACTCAC-3' (SEQ ID NO: 10).

Introduction of amino acid substitutions into murine and human GPIIIa plasmids—The cDNA expression vector, pCMV3-mouse ITGB3, encoding murine GPIIIa, was purchased from Creative Biogene (Shirley, N.Y.). Nucleotide substitutions were introduced into this plasmid using a Quick-Change site-directed mutagenesis kit (Stratagene, La Jolla, Calif.) to convert $T_{30} \rightarrow A$, $S_{32} \rightarrow P$, $Q_{33} \rightarrow L$, and $N_{39} \rightarrow D$, resulting in a plasmid encoding murine GPIIIa containing a completely humanized PSI domain, termed APLD murine GPIIIa. Using this as a template, additional mutations were introduced in the codons encoding $M_{470}$ and $P_{446}$ within the murine EGF1 domain to humanize them to $Q_{470}$ and $H_{446}$, respectively, with the resulting constructs referred to as APLDQ, APLDH, and APLDQH. Conversely, $G_{463}P_{464} \rightarrow DQ$, $H_{446} \rightarrow P$, and $Q_{470} \rightarrow M$ mutations were introduced into the human ITGB3 expression vector, pcDNA3-human ITGB3 to generate plasmids encoding human GPIIIa with $D_{463}Q_{464}$, $P_{446}$, or $M_{470}$ within the human EGF1 domain. Primers used to introduce these mutations are listed in Table 1. All constructs and mutations were confirmed by nucleotide sequencing.

Flow cytometry—Flow cytometry analysis of antibody binding to transiently-transfected HEK293 cells was performed 48 hours post-transfection using a FACSCanto II or an Accuri C6 flow cytometer (BD Biosciences). Non-transfected cells were used as negative control. Antibody binding was detected using FITC-labeled goat (Fab')$_2$ anti-human IgG, FITC-labeled goat (Fab')$_2$ anti-mouse IgG, as appropriate. Data were analyzed using FlowJo software (Tree Star Inc., Ashland, Oreg.).

Inhibition of PAC-1 binding to human $\alpha_{IIb}\beta_3$ by anti-HPA-1a alloantibodies—HEK293FT cells were transfected with wild-type human αIIbβ3 plus EGFP. The cells were pre-incubated with mAbs SZ21, B2G1, or 26.4 at 2.5 µg/ml, or with purified total IgG from normal control, PTP or FNAIT samples at a 1:50 dilution at room temperature for 30 min, and then incubated for another 30 min after adding 2.5 µg/ml PAC-1 with 0.2 mM $Ca^{+2}$ and 2 mM $Mn^{+2}$. The cells were stained separately with the murine mAb, AP3, to detect total $\beta_3$ surface expression to be able to normalize the binding and competition data. EGFP-positive cells were analyzed by flow cytometry after staining with Alexa Fluor 647-conjugated goat anti-mouse IgM (for PAC-1) or Alexa Fluor 647-conjugated goat anti-mouse IgG (for AP3). The mean fluorescence intensity (MFI) of PAC-1 binding was

TABLE 1

Oligonucleotide primers used for site-directed mutagenesis

| | Mutations | Orientation | Primer sequence |
|---|---|---|---|
| Mouse GPIIIa | T30A S32PQ33L | Forward | 5'-gtgctcagatgagGcCttgCctcTgggctcaccccgatg-3' (SEQ ID NO: 11) |
| | | Reverse | 5'-catcggggtgagcccAgagGcaaGgCctcatctgagcac-3' (SEQ ID NO: 12) |
| | N39D | Forward | 5'-gggctcaccccgatgtGacctgaaggagaacctg-3' (SEQ ID NO: 13) |
| | | Reverse | 5'-caggttctccttcaggtCacatcggggtgagccc-3' (SEQ ID NO: 14) |
| | M470Q | Forward | 5'-gaccagggctggctggggtccAgtgtgagtgctctgaggagg-3' (SEQ ID NO: 15) |
| | | Reverse | 5'-cctcctcagagcactcacacTGggaccccagccagccctggtc-3' (SEQ ID NO: 16) |
| | P446H | Forward | 5'-gaccccagccagccagggccACagcggcacac-3' (SEQ ID NO: 17) |
| | | Reverse | 5'-ggtgtgccgctGTggccctggctggctggggtcc-3' (SEQ ID NO: 18) |
| Human GPIIIa | Q470M | Forward | 5'-gggcctggctggctgggatccATGtgtgagtgctcagaggaggac-3' (SEQ ID NO: 19) |
| | | Reverse | 5'-gtcctcctctgagcactcacaCATggatcccagccagccaggccc-3' (SEQ ID NO: 20) |
| | H446P | Forward | 5'-ctgaacctaatagccCtcgctgcaacaatgg-3' (SEQ ID NO: 21) |
| | | Reverse | 5'-ccattgttgcagcgaGggctattaggttcag-3' (SEQ ID NO: 22) |
| | G463D P464Q | Forward | 5'-gtggggtatgccgttgtgACcAGggctggctgggatcccag-3' (SEQ ID NO: 23) |
| | | Reverse | 5'-ctgggatcccagccagccCTgGTcacaacggcatacccccac-3' (SEQ ID NO: 24) |

Altered sequences are in bold.

Altered sequences are in bold.

Expression of wild-type and mutant αIIbβ3 isoforms—HEK 293FT cells were transfected with a plasmid encoding human αIIb together with a plasmid encoding wild-type or mutant forms of murine or human GPIIIa. HEK 293FT cells were grown in 6-well plates in DMEM containing 10% FBS without antibiotics one day before transfection to obtain 80-90% confluency at the time of transfection. Cells were transfected with 1 µg of each plasmid and 5 µL of Lipofectamine 2000 (Invitrogen) in 250 µL of Opti-MEM I Reduced Serum Medium. Following transfection, cells were grown for an additional 48 h at 37° C. to allow for protein expression.

normalized to β3 expression and presented as a percentage of control in the absence of anti-HPA-1a alloantibodies.

Modified antigen capture enzyme-linked immunosorbent assay—8×10$^7$ washed human or murine platelets were incubated at room temperature for 1 hr. with human FNAIT alloantisera that had been diluted 1:5, washed, and then lysed in 200 µl ice-cold lysis buffer [20 mM Tris (pH7.4), 150 mM NaCl, 1% Triton X-100, 1 mM ethylenediaminetetraacetic acid, 10 mM N-ethylmaleimide], containing a protease inhibitor cocktail (Thermo Fisher Scientific, Waltham, Mass.). Lysates were added to microtiter wells that had been coated with anti-mouse CD41 (eBioscience, San Diego, Calif.) to capture immune complexes from mouse platelets, or mAb AP2 to capture immune complexes from human platelets. Bound immune complexes were detected using alkaline phosphatase-conjugated anti-human IgG (Jackson ImmunoResearch Laboratories, West Grove, Pa.).

Molecular modeling and docking—The model of the variable region of B2G1 Fab was generated using the Rosetta Antibody Protocol[25-29]. The structures of the PSI and I-EGF1 domains from the crystal structure of αIIbβ3[30] (PDB code: 3FCS) were docked into the CDR loop regions of antibody B2G1 using the ClusPro protein-protein docking server[31-35]. Residues A30, P32 and L33 were defined as the docking sites on integrin β3. Non-complementarity-determining regions were automatically masked using 'Antibody mode'[36].

Statistics—Data shown are mean±SEM. Statistical comparisons were made using an unpaired, two-tailed Student's t test. Differences were considered statistically significant at P<0.05.

Results

Recreating the HPA-1a epitope in the PSI domain of murine platelet GPIIIa—As illustrated in FIGS. 1A-1B and FIG. 2A, polymorphic amino acid $Leu_{33}$ is located at the end of a long flexible loop extending from the PSI domain of GPIIIa. Previous studies incorporating a series of amino acid substitutions into a small construct comprised of murine GPIIIa N-terminal residues 1-66 demonstrated that humanizing T30A, S32P, Q33L, and N39D (shown schematically in FIG. 2A) is required to reconstitute binding of the Type I, HPA-1a-selective mAb, SZ21, and at least several human polyclonal anti-HPA-1a alloantisera[37]. Based on these data, a CRISPR strategy was devised (FIG. 2B) to introduce a repair template into exon 3 of the murine ITGB3 locus that would encode these four amino acid substitutions. From 60 zygotes microinjected with a plasmid construct (FIG. 2C) encoding the gRNA shown in FIG. 2B, the Cas9 endonuclease, and the APLD HDR template, one female offspring gave the appropriately confirmed genotype (FIG. 2D-2F), and was designated the APLD mouse.

Figures 3A, 3B:
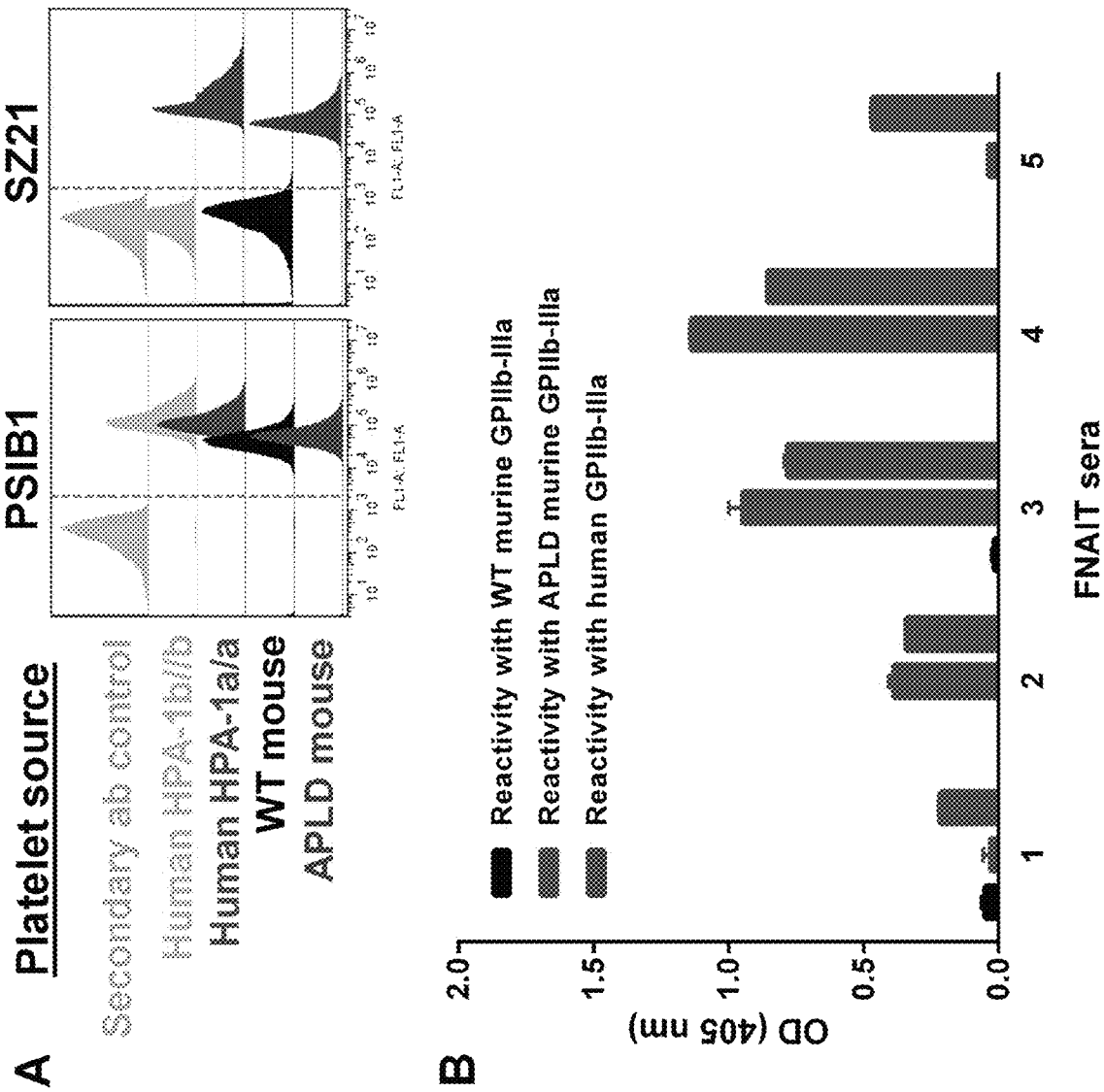
FIGS. 3A-3B show the APLD humanized murine PSI domain supports the binding of many, but not all, human anti-HPA-1a alloantisera.
Figure 7:
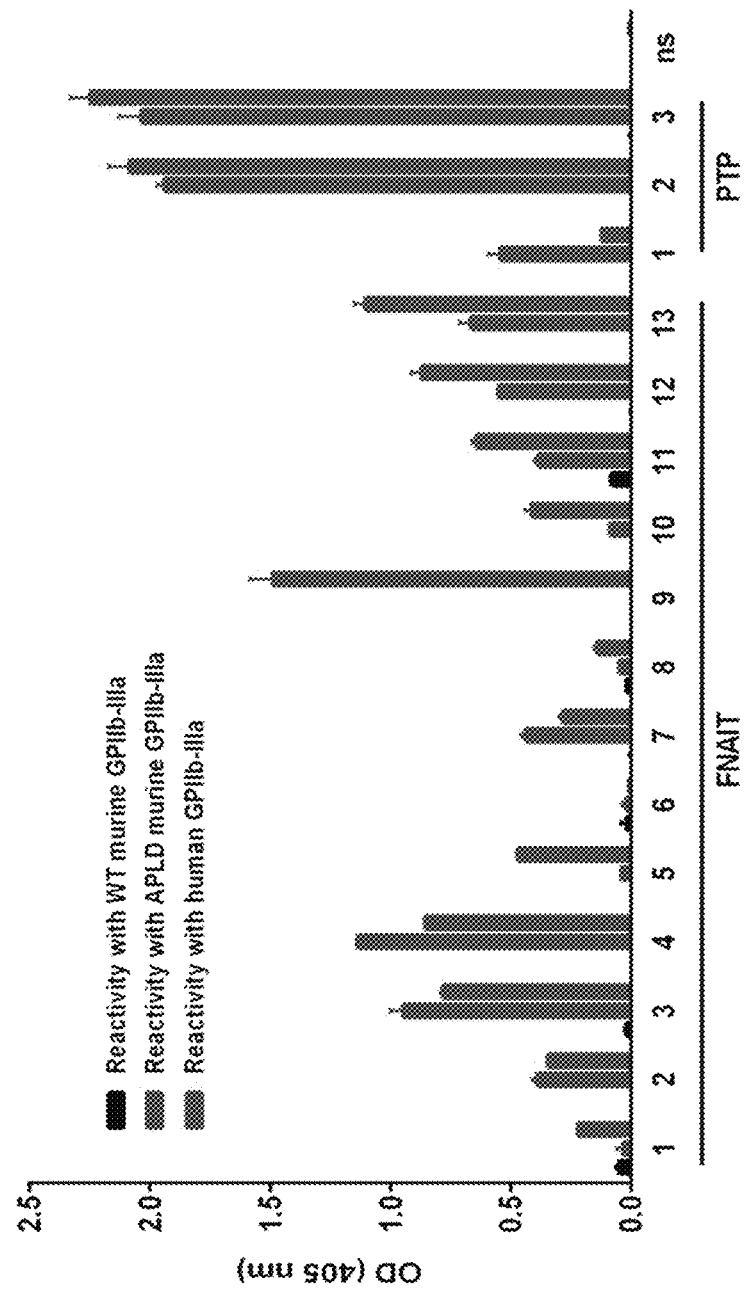
FIG. 7 shows antigen-capture ELISA analysis of anti-HPA-1a maternal alloantisera binding to human and murine forms of GPIIb-IIIa. Sixteen different human FNAIT alloantisera or PTP alloantisera were incubated with human or murine platelets of the indicated phenotype. Platelet/antibody complexes were then detergent lysed and added to microtiter wells that had been coated with either anti-mouse CD41 to capture immune complexes from mouse platelets, or mAb AP2 to capture immune complexes from human platelets. Note that human FNAIT alloantisera 2, 3, 4, 7, 11, 12, 13 and PTP alloantisera 2 and 3 react similarly with human GPIIb-IIIa and APLD murine GPIIb-IIIa, while human FNAIT alloantisera 1, 5, 9, 10 react poorly with murine APLD GPIIb-IIIa, suggesting that the preponderance of the HPA-1a-specific alloantibodies present in these polyclonal sera have more complex epitope requirements. None of the FNAIT alloantisera react with wild-type murine GPIIb-IIIa, as expected.

Specific amino acids within the EGF1 domain of GPIIIa are required to support the binding of Type II HPA-1a antibodies—Previous studies have shown that the immune response to HPA-1a is both polyclonal and heterogeneous, with some alloantisera containing subpopulations that require, in addition to polymorphic amino acid 33, discontinuous sequences within still-to-be-characterized regions of the linearly distant EGF1 domain[19,38]. As shown in FIG. 3A, the prototypical Type I HPA-1a-specific mAb, SZ21, binds readily to APLD, but not wild-type, murine GPIIIa (muGPIIIa), confirming re-creation of its epitope within the murine PSI domain. To gain further insight into the structural requirements necessary for the binding of antibody populations likely to exist in more complex polyclonal human maternal anti-HPA-1a alloantisera, we examined the ability of five different human FNAIT alloantisera to bind to muGPIIIa, APLD muGPIIIa, or human GPIIIa that had been immobilized in microtiter wells. As shown in FIG. 3B, three of the five representative alloantisera reacted with APLD muGPIIIa, whereas two others did not, consistent with the notion that these alloantisera contain a preponderance of so-called Type II anti-HPA-1a alloantibodies[19] that require residues outside the humanized PSI domain for their binding. The reactivities and specificities of additional human anti-HPA-1a alloantisera are shown in FIG. 7.

Figure 4A:
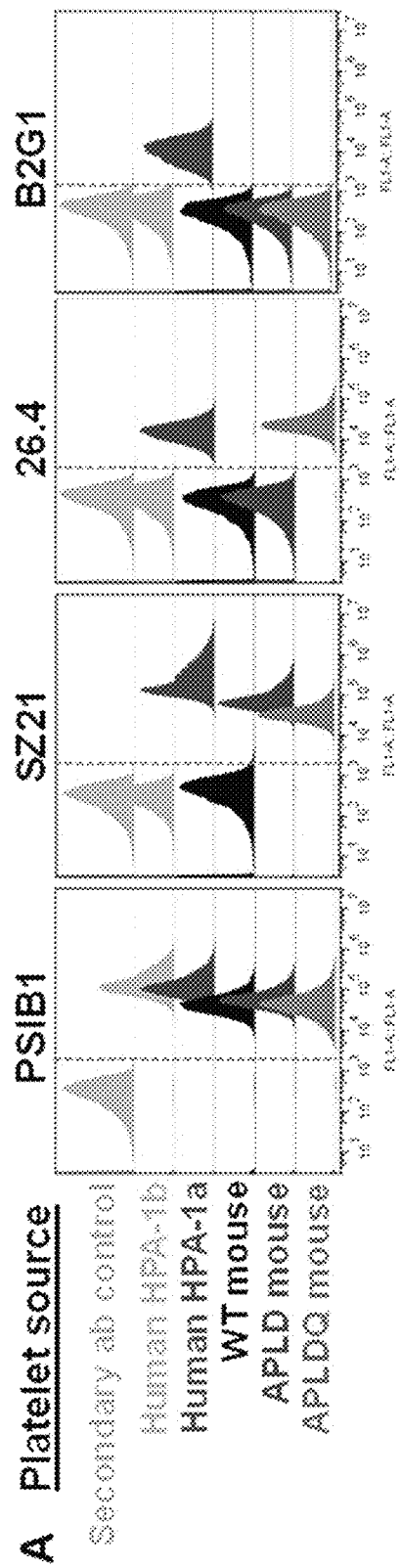
FIGS. 4A-4B show structural requirements for binding of Type II anti-HPA-1a antibodies.
Figure 4B:
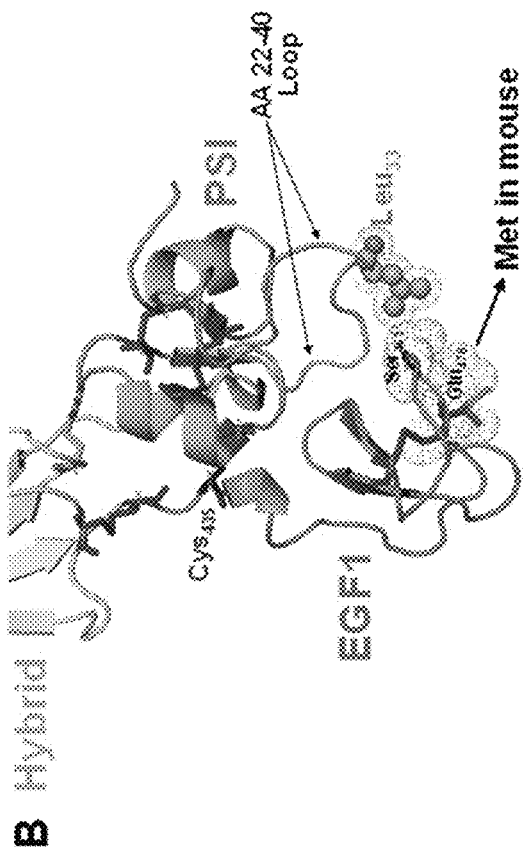

To determine the structural requirements for binding of Type II anti-HPA-1a antibodies, we examined the binding of the prototypical Type II antibody, mAb 26.4, to murine APLD platelets. As shown in FIG. 4A, similar to human alloantiseras 1 and 5 in FIG. 3B, mAb 26.4 was unable to bind murine platelets expressing APLD GPIIIa. Close examination of the interface between the PSI and EGF1 domain (FIG. 4B) revealed that a loop extending out from the EGF1 domain of human GPIIIa brings amino acid $Q_{470}$ into close proximity with polymorphic residue Leu33. This residue is a methionine in murine GPIIIa ($Ser_{469}$ is conserved in both species). To determine whether $Q_{470}$ forms a part of the epitope recognized by Type II anti-HPA-1a antibodies, we further modified the sequence of murine GPIIIa, starting with our APLD mouse, by introducing an HDR that would change $M_{470} \rightarrow Q$ (see methods) in the murine EGF1 domain. mAb 26.4 now bound readily to platelets from this second generation HPA-1a humanized transgenic mouse, which we designated the APLDQ mouse (FIG. 4A). In contrast, the binding of mAb SZ21 was not enhanced by additional humanization of the EGF1 domain, consistent with its being classified as a Type I antibody whose epitope is entirely contained within the PSI domain. Unexpectedly, platelets from the APLDQ mouse were completely unreactive with an HPA-1a-specific mAb, termed B2G1, that had been isolated by phage display from an HPA-1a allo-immunized woman[22], demonstrating additional unsuspected complexity in the specificities of antibody subpopulations that can exist in polyclonal maternal anti-HPA-1a alloantisera.

Figures 5A, 5B, 5C:
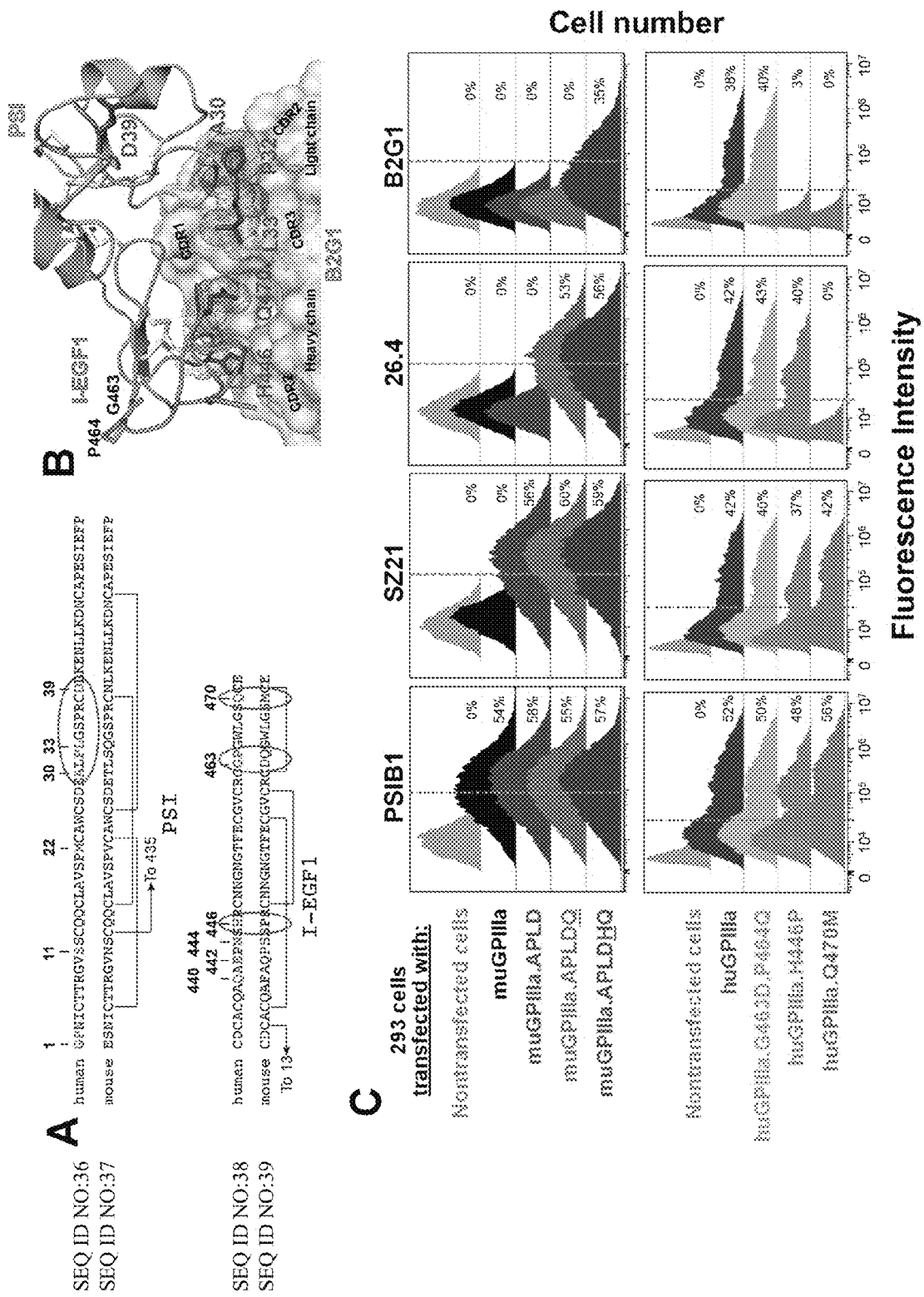
FIGS. 5A-5C show multiple amino acids within I-EGF1 can contribute to the binding of type II anti-HPA-1a antibodies.

FIG. 5A highlights the amino acid differences between the murine versus human PSI and EGF1 domains of GPIIIa. As shown, in addition to the Q470M difference that is spatially close to polymorphic residue 33, there are six additional amino acid differences in EGF1 between the two species. Molecular docking analysis of B2G1 with the EGF1 and PSI domains of GPIIIa (FIG. 5B) revealed that of these seven amino acids, only $H_{446}$ and $Q_{470}$ are predicted to be at the antibody/antigen interface together with $L_{33}$. Accordingly, expression of an APLDQ isoform of murine GPIIIa with an additional $Pro_{446} \rightarrow His$ amino acid substitution supported B2G1 binding. Conversely, substituting human $H_{446}$ with a proline residue resulted in complete loss of B2G1 binding, while both B2G1 and mAb 26.4 lost reactivity with human GPIIIa if $Q_{470}$ was substituted with a methionine residue. In contrast, none of HPA-1a-specific antibodies were affected by mutation of G463D and P464Q (FIG. 5C), consistent with them not being present at the antibody/antigen interface (FIG. 5B). Taken together, these data demonstrate that a variable number of spatially-close, non-polymorphic, amino acids form multiple epitopes, each centered around polymorphic residue 33, that together comprise the target recognition sites recognized by polyclonal antibody subpopulations present in anti-HPA-1a antisera.

Discussion

Early studies aimed at characterizing the molecular nature of the HPA-1a epitope found that tryptic or chymotryptic proteolytic fragments of GPIIIa, ranging from 17 kDa[39] to 66 kDa[40] in size, could bind HPA-1a-specific alloantibodies. Later studies by Beer and Coller[41] found that the 66 kDa polypeptide is comprised of the 17 kDa amino terminal fragment of GPIIIa (now known to contain the PSI domain) disulfide bonded to a larger 50 kDa fragment containing residues 348-654 (now known to contain the EGF1 domain). Following the discovery that the formation of the HPA-1a epitope is controlled by a Leu33Pro amino acid substitution at the amino terminus of GPIIIa[13,14], small synthetic peptides surrounding this polymorphic residue were synthesized, but were unable to bind HPA-1a alloantibodies[42], likely due to the inability of linear peptides to fold and adopt the proper tertiary conformation, as there are seven cysteine residues within the first 55 amino acids of GPIIIa that form a complex disulfide-bonded knot-like structure. Interestingly, a somewhat larger recombinant protein comprised of the first 66 amino acids of GPIIIa (i.e. the entire PSI domain) produced in prokaryotic λgt22 bacteriophage plaques was able to react with four different anti-HPA-1a sera from PTP patients[43], thereby localizing the HPA-1a epitope to the amino terminal 7 kDa of GPIIIa surrounding polymorphic amino acid 33.

Two studies published in the mid-1990s revealed that the HPA-1 epitope recognized by a subset of HPA-1a antibodies might be more complex. Valentin et al. used site-directed mutagenesis to disrupt the disulfide bond linking the PSI domain to the EGF1 domain of GPIIIa, and found that while some anti-HPA-1a alloantibodies continued to bind well, nearly a third lost some or all reactivity with the mutant protein[19]. Based on these findings, the authors proposed that HPA-1a antibodies can be classified as Type I or Type II based upon their dependence on noncontiguous linear sequences present in the PSI and EGF1 domains. This concept was supported by the work of Stafford and colleagues[44], who found that ~20% of 121 maternal anti-HPA-1a alloantibodies reacted with recombinant fragments of GPIIIa only when the fragment contained both the PSI and EGF1 domains. Honda and colleagues[38] detected the presence of Type II antibodies that reacted with chimeric proteins comprised of *Xenopus* GPIIIa molecules containing various patches of human GPIIIa sequences only when the *Xenopus* protein contained human amino acids 26-38 as well as amino acids 287-490.

Figure 8:
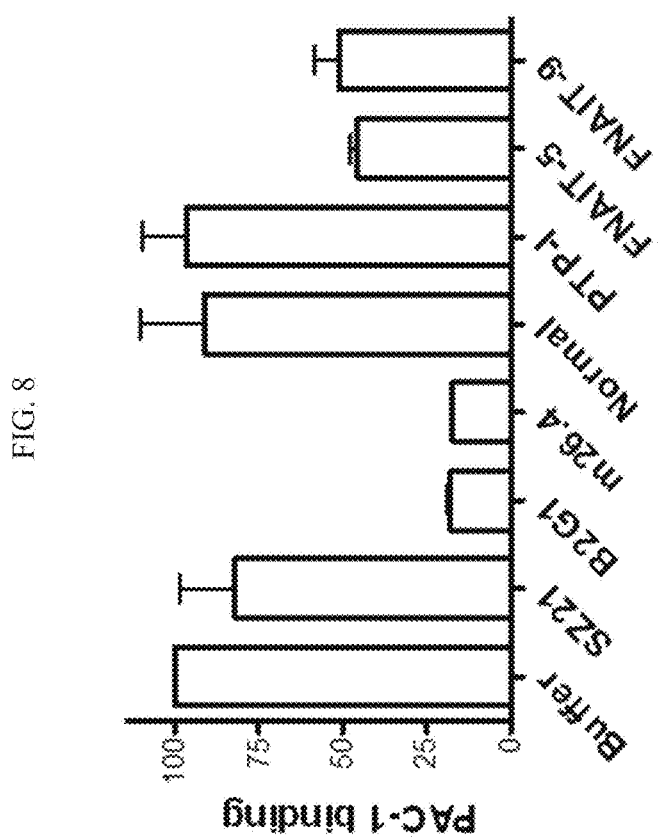
FIG. 8 shows inhibition of PAC-1 binding to human αIIbβ3 by Type II, but not Type I, anti-HPA-1a alloantibodies. HEK293FT cells were transfected with wild-type human αIIbβ3 plus EGFP. Cells were pre-incubated with either the Type I mAbs SZ21, the Type II mAbs B2G1 and 26.4, or purified IgG fractions from a previously-characterized Type I PTP antisera (PTP-1), or previously characterized Type II FNAIT antisera (FNAIT-5 and FNAIT-9). Following pre-incubation, the fibrinogen ligand-mimetic mAb PAC-1 was added in a buffer containing 0.2 mM $Ca^{+2}$ and 2 mM $Mn^{+2}$. EGFP-positive cells were analyzed by flow cytometry for the binding of PAC-1. PAC-1 binding was normalized to total β3 surface expression and presented as a percentage of buffer control. Data are mean±SD (n≥2). Note that both monoclonal and polyclonal Type II antibodies inhibit PAC-1 binding to various extents, while Type I antibodies are largely without effect.
Figure 9:
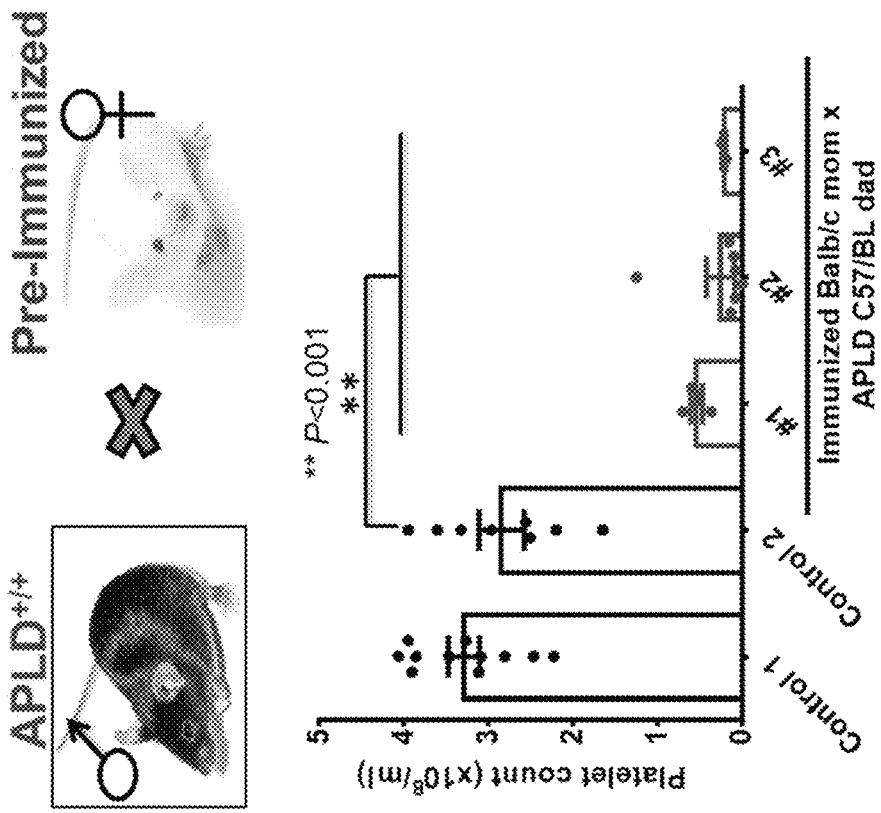
FIG. 9 shows pre-immunized wild-type females bred with APLD[+/+] males give birth to severely thrombocytopenic pups Breeding control #1 is a WT non-immunized Balb/c female crossed with an APLD C57BL/6 male. Breeding control #2 is an immunized Balb/c female crossed with a WT C57BL/6 male.
Figures 10A, 10B, 10C, 10D:
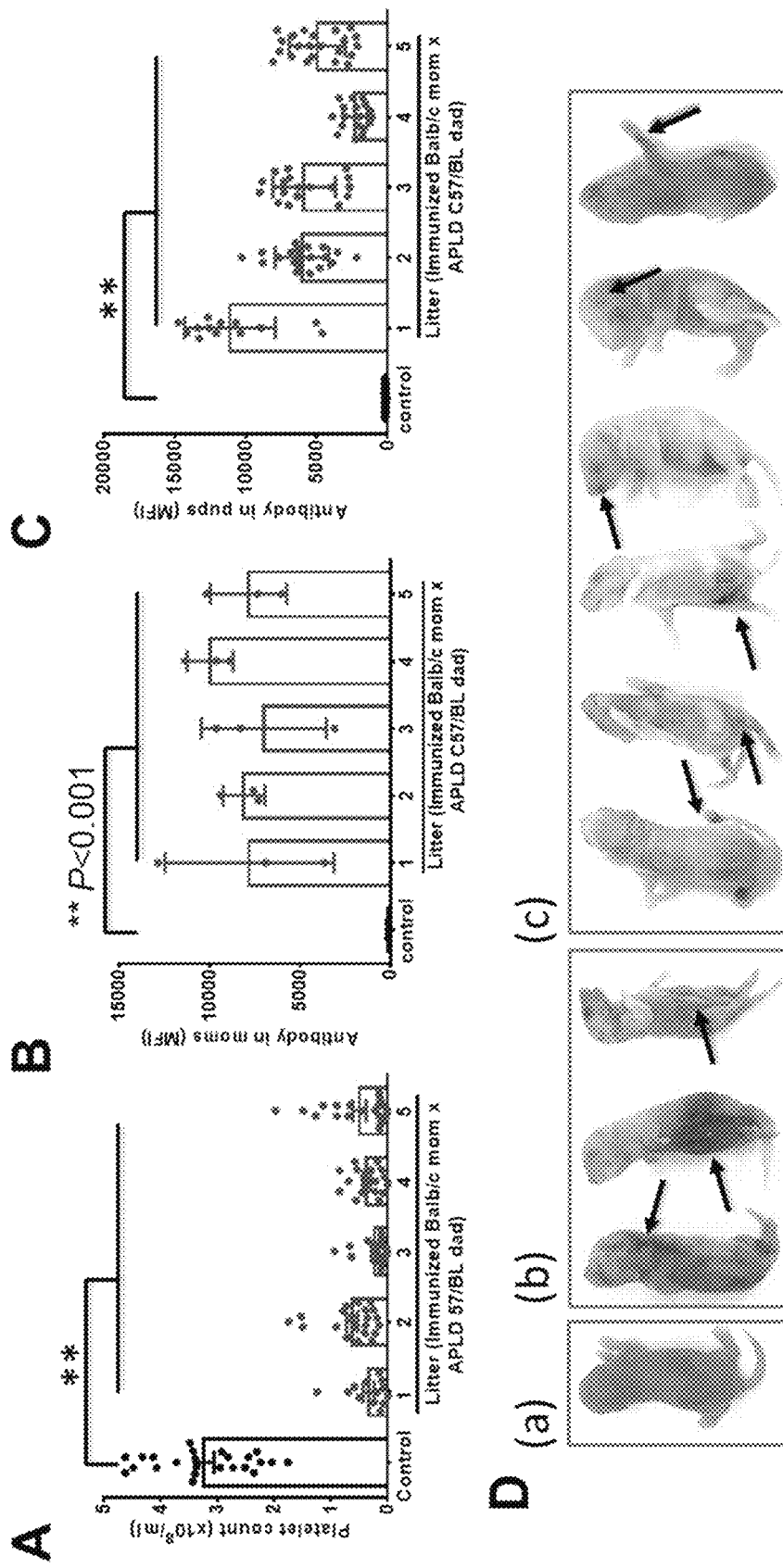
FIGS. 10A-10D show that although the female was allo-immunized only once, fetal/neonatal thrombocytopenia persists for at least five subsequent pregnancies. Maternal anti-APLD β3 integrin antibodies cause thrombocytopenia and bleeding in the pups.
Figure 11:
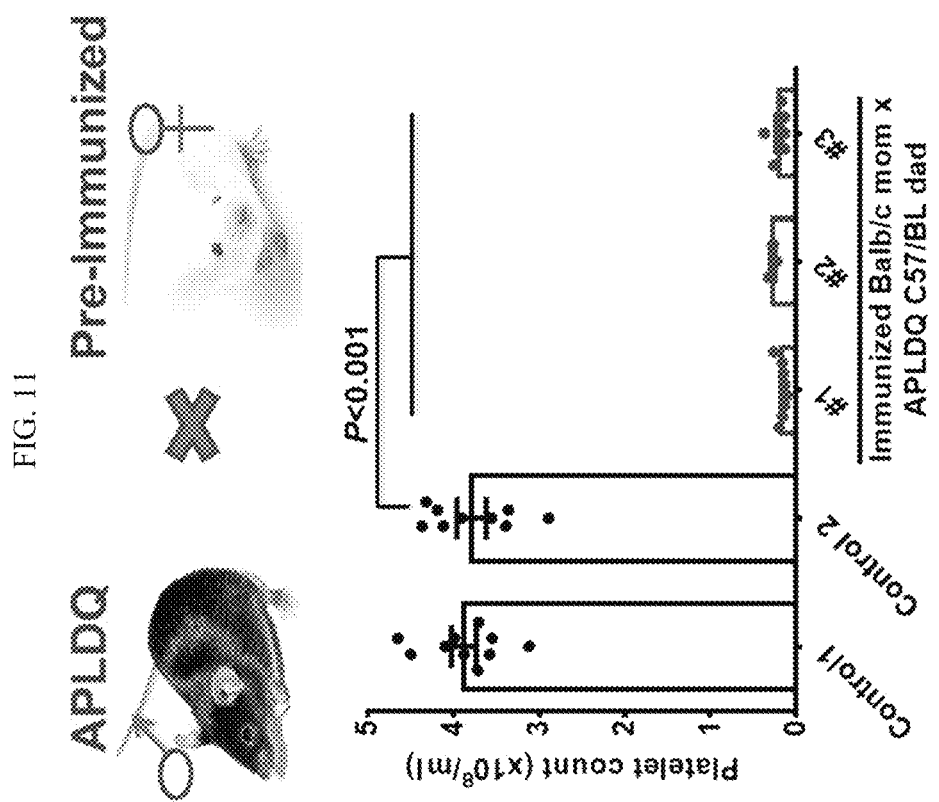
FIG. 11 shows that, similar to the APLD model shown in FIG. 9, pre-immunized wild-type females bred with APLDQ males give birth to severely thrombocytopenic pups. Breeding control #1 is a WT non-immunized Balb/c female crossed with an APLD C57BL/6 male. Breeding control #2 is an immunized Balb/c female crossed with a WT C57BL/6 male.
Figures 12A, 12B, 12C, 12D:
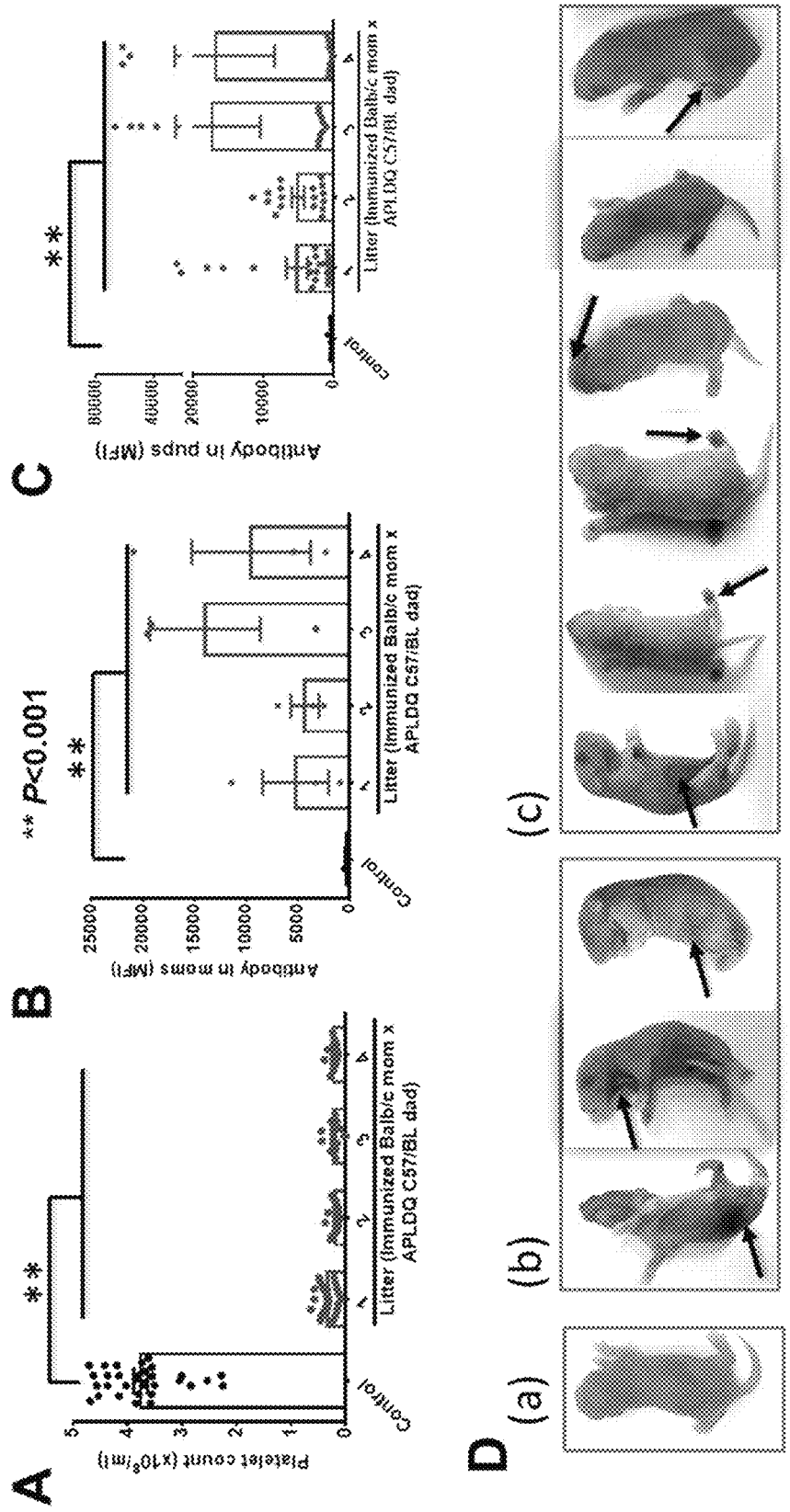
FIGS. 12A-12D shows that thrombocytopenia and bleeding in the pups persists in up to 4 pregnancies in the breeding outlined in FIG. 11. Maternal anti-APLD β3 integrin antibodies cause thrombocytopenia and bleeding in the pups.

Epitopes as viewed from the perspective of the antibody: HPA-1a antibody titer alone has not consistently been found to correlate with the severity of clinical outcome[45,46], and additionally dividing HPA-1a-specific alloantibodies into Types I versus Type II disappointingly provided neither a diagnostic nor prognostic advantage[44]. Recently, however, Santoso and colleagues reported that a specific population of anti-HPA-1a alloantibodies preferentially bind GPIIIa when it is complexed with the αv, rather than αIIb, integrin subunit, present on endothelial cells, and that such antibodies are strongly associated with the development of intracranial hemorrhage in FNAIT[47]. These findings have several important implications. First, they strongly suggest that identifying, and distinguishing between, distinct populations of anti-HPA-1a antibodies that invariably exist within all maternal polyclonal anti-HPA-1a antisera may be the key for predicting the risk of thrombocytopenia and bleeding in cases of FNAIT. Second, they demonstrate that the influence of the local conformation surrounding polymorphic amino acid residue 33 has a profound effect on determining the core target recognition site for alloantibody binding and its subsequent effector consequences. Our finding that the binding of two different Type II monoclonal anti-HPA-1a antibodies can be distinguished from one another by their requirement for distinct amino acids within the EGF1 domain of GPIIIa (FIGS. 5A-5C) lends further support to the notion that antibody/epitope recognition involves more than simply the polymorphic amino acid, and likely varies among antibody subpopulations that comprise virtually any alloimmune response. Mapping the polyclonal immune response to HPA-1a using cells expressing murine GPIIIa containing specific mouse→human amino acid substitutions, together with the growing number of HPA-1a-specific monoclonal antibodies, may enable high-resolution analysis of alloantibody subpopulations to provide a predictive diagnostic benefit. Interestingly, preliminary studies (FIG. 8) indicate that Type I and Type II alloantibody populations have distinct effects on the ability of platelets to interact with their ligand. Whereas Type I antibodies have only minimal effects, Type II antibodies significantly block the binding of the fibrinogen mimetic, PAC-1, to the GPIIb-IIIa complex, perhaps by restraining extension of GPIIIa during the integrin activation process.[48] Additional studies in this regard are the subject of an extensive planned clinical investigation.

That individual antibody populations within a given polyclonal serum have different surface topographical requirements explains why they are able to induce varying pathophysiological effects. In the world of histocompatibility testing, there is growing evidence that, in addition to genotypic matching of cell surface antigens, phenotypic determination of the antibody/epitope repertoire of the recipient, including for those epitopes contributed by residues in discontinuous positons that cluster together on the molecular surface, may be important predictors of transplant success[49]. Structure-based matching has already been validated as a strategy to improve platelet transfusion support in refractory thrombocytopenic patients[50,51]. It is possible, therefore, that precision medicine-based diagnostic regimens that consider not only polymorphic differences, but also the contact areas of alloantibody subpopulations, will be needed in order to offer a more precise dissection of the polyclonal nature of the immune response, allowing one to more accurately predict the risk of thrombocytopenia, bleeding, and intracranial hemorrhage.

The polyclonal nature of the response generated by the clinically important Leu33Pro polymorphism in GPIIIa is complex, and remains a fascinating area of investigation with implications for both prophylaxis and therapy. Given the polyclonal nature of HPA-1-specific antibodies, and the likelihood that any maternal antiserum contains antibodies that come at polymorphic amino acid 33 from different angles and bind with different topographical distributions and with different affinities due to the involvement of additional residues, we suspect that a mixture of HPA-1-specific mAbs, rather than any single one, may be required to block the binding of polyclonal maternal antibodies and prevent clearance of fetal platelets from circulation. Identification of two residues ($H_{446}$ and $Q_{470}$) within EGF1 as both necessary and sufficient for binding of the Type II anti-HPA-1a alloantibody does not rule out the possibility that residues within or outside of EGF1 might be required to support the binding of still-to-be-characterized Type II alloantibodies. For example, $D_{39}$ within the PSI domain, and $R_{93}$ at the hybrid/PSI interface both have been reported to affect the binding of human anti-HPA-1a antibodies[37,52], while other antibodies are specific for the bent conformation of the integrin, likely due to their requirement for both the PSI and EGF1 domains, as described in this study.[53] Our atomic-level dissection demonstrating an increasingly wide range of antibody subpopulations present within the alloantisera of HPA-1a-alloimmunized individuals highlights the challenge of developing single reagents with narrow epitope specificities to inhibit alloantibody-mediated platelet destruction. Prophylactic delivery of humanized anti-HPA-1a-specific mAbs, introduced into the maternal circulation during pregnancy or shortly following childbirth, could be used to clear neonatal platelets that have passed through the mother, thereby preventing or lessening development of the alloimmune response in the first place.

Example 2

Figure 13:
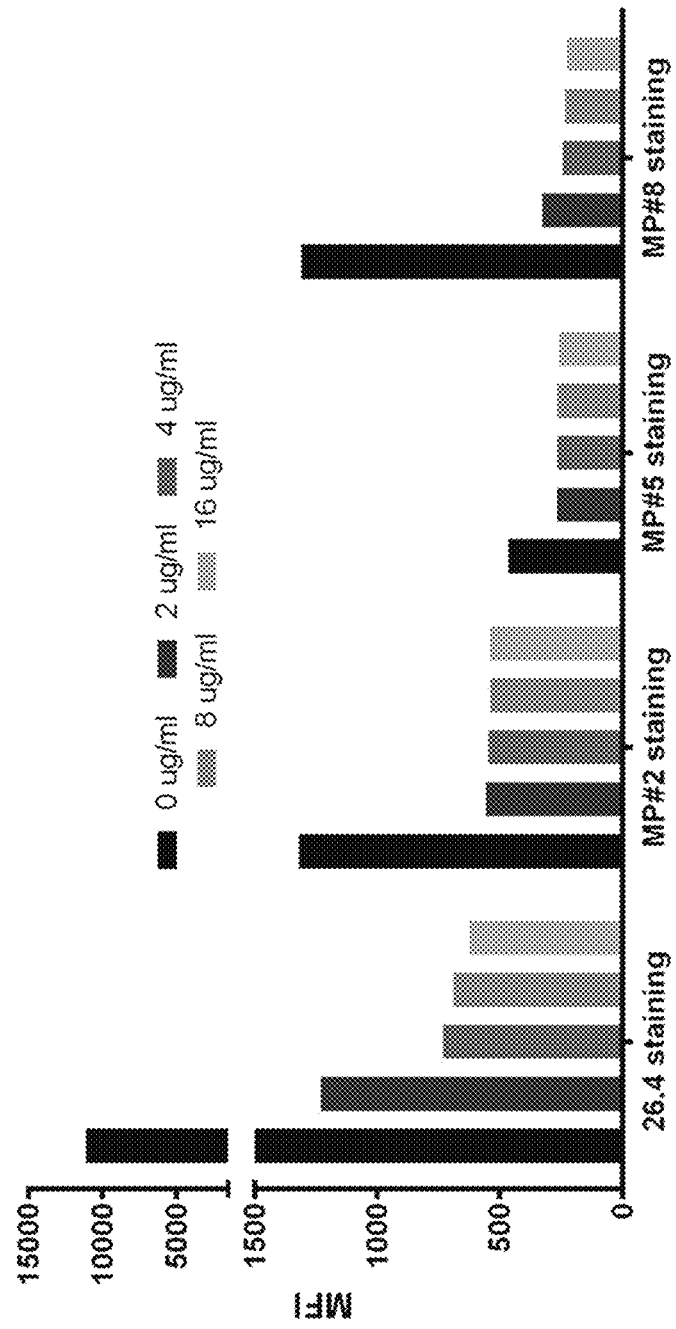
FIG. 13 shows that 4 μg/ml mAb 26.4 efficiently inhibits the binding of murine polyclonal anti-APLDQ antibodies to mouse APLDQ platelets in vitro. All concentrations tested between 2 μg/ml and 16 μg/ml effectively inhibited binding.

Intraperitoneal injection of an anti-HPA-1a mAb induced severe thrombocytopenia in APLDQ mice, but not wild-type mice. Furthermore, platelets from APLDQ mice, when introduced into wild-type mice, elicited a strong polyclonal immune response that was specific for, and importantly restricted to, the epitopes created by these humanized residues, demonstrating that the APLDQ humanized form of murine GPIIIa is immunogenic in mice. Wild-type female mice pre-immunized with APLDQ platelets and bred with APLDQ male mice, gave birth to severely thrombocytopenic pups, many of whom exhibited an accompanying bleeding phenotype (FIGS. 11 and 12A-12D). However, mAb 26.4 efficiently inhibits the binding of murine polyclonal anti-APLDQ antibodies to mouse APLDQ platelets (FIG. 13).

IVIG (Intravenous immunoglobulin) is a highly purified globulin preparation obtained from the pooled plasma of between 1000 and 15,000 healthy donors per batch. IVIG targets the cellular immune compartment at multiple levels, including innate and adaptive immune cells. IVIG interacts with dendritic cells, macrophages, and granulocytes, mainly via activating and inhibitory FcγRs. The first maternal infusion of IVIG for the treatment of FNAIT was reported in 1988 (Bussel J B, et al. New Engl J Med. 1988;319(21): 1374-8), after which IVIG rapidly gained ground as a standard antenatal treatment strategy for FNAIT. A recent systematic review suggests that weekly IVIG administration, with or without the addition of corticosteroids, is the first-line antenatal management in FNAIT, and helps reduce or alleviate the effects of FNAIT in infants and reduce the severity of thrombocytopenia (Dian Winkelhorst, et al. BLOOD.2017; 129(11):1538-1547).

Figure 14:
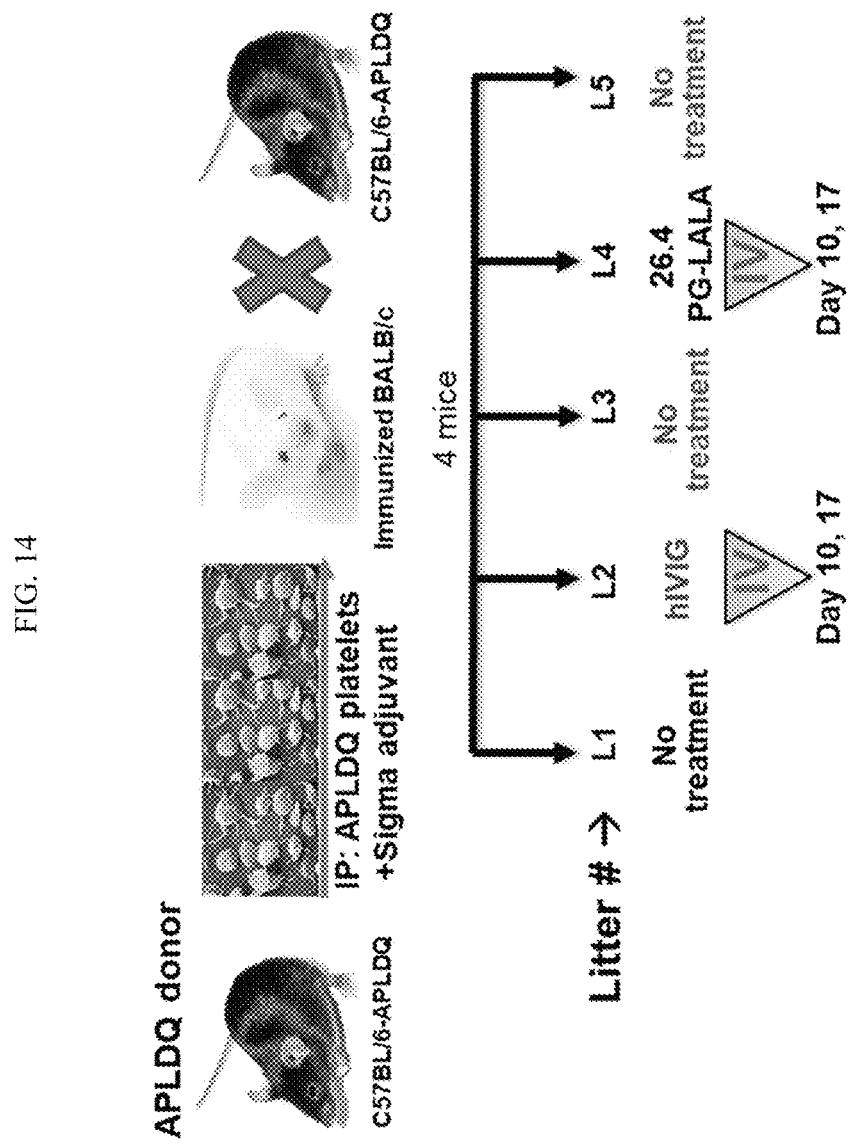
FIG. 14 shows the IVIG and mAb 26.4 treatment protocols. Treatment with human IVIG at 1 g/kg, introduced IV at days 10 and 17 post-mating elevates platelet counts of pups born to APLDQ alloimmunized females. Likewise, treatment with the PG-LALA form of mAb 26.4 at 30 μg/mouse introduced at days 10 and 17 post-mating elevates platelet counts of pups born to APLDQ alloimmunized females.
Figure 15:
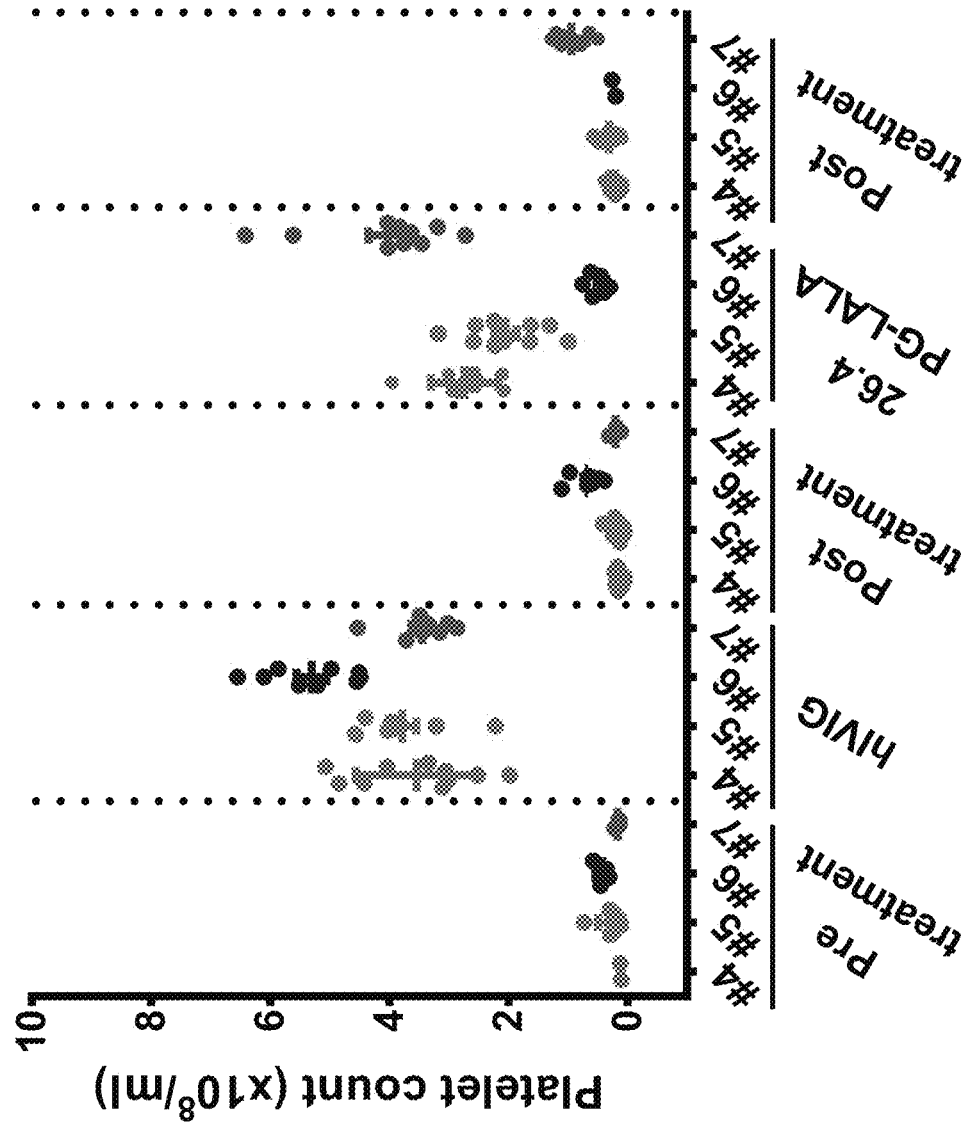
FIG. 15 shows that both IVIG and PG-LALA 26.4 effectively elevate the platelet count in pups of APLDQ alloimmunized female mice.

Administration of intravenous immunoglobulin G (IVIG) or mAb 26.4 into pregnant female mice at days 10 and 17 post-mating lowered the concentration of anti-APLDQ alloantibodies in both the maternal and fetal circulation, and importantly normalized the platelet count in the pups (FIGS. 14 and 15). Taken together, these data establish a novel murine model of FNAIT that recapitulates many of the clinically important features of FNAIT.

REFERENCES

1. Newman P J, McFarland J G, Aster R H. The Alloimmune Thrombocytopenias. In: Loscalzo J, Schafer A I, eds. Thrombosis and Hemorrhage: Lippincott Williams and Wilkins; 2003:441-456.
2. Williamson L M, Hackett G, Rennie J, et al. The natural history of fetomaternal alloimmunization to the platelet-specific antigen HPA-1a (PlA1, Zwa) as determined by antenatal screening. Blood. 1998; 92(7):2280-2287.
3. Kjeldsen-Kragh J, Killie M K, Tomter G, et al. A screening and intervention program aimed to reduce mortality and serious morbidity associated with severe neonatal alloimmune thrombocytopenia. Blood. 2007; 110 (3):833-839.
4. Bussel J. Diagnosis and management of the fetus and neonate with alloimmune thrombocytopenia. J Thromb Haemost. 2009; 7 Suppl 1:253-257.
5. Giovangrandi Y, Daffos F, Kaplan C, Forestier F, Mac A J, Moirot M. Very early intracranial haemorrhage in alloimmune fetal thrombocytopenia. Lancet. 1990; 336 (8710):310.
6. Mueller-Eckhardt C, Kiefel V, Grubert A, et al. 348 cases of suspected neonatal alloimmune thrombocytopenia. Lancet. 1989; 1:363-366.
7. Bonacossa I A, Jocelyn L J. Alloimmune thrombocytopenia of the newborn: neurodevelopmental sequelae. Am J Perinatol. 1996; 13(4):211-215.
8. Dreyfus M, Kaplan C, Verdy E, Schlegel N, Durand-Zaleski I, Tchernia G. Frequency of immune thrombocytopenia in newborns: a prospective study. Immune Thrombocytopenia Working Group. Blood. 1997; 89(12): 4402-4406.
9. Spencer J A, Burrows R F. Feto-maternal alloimmune thrombocytopenia: a literature review and statistical analysis. Aust N Z J Obstet Gynaecol. 2001; 41(1):45-55.
10. Turner M L, Bessos H, Fagge T, et al. Prospective epidemiologic study of the outcome and cost-effectiveness of antenatal screening to detect neonatal alloimmune thrombocytopenia due to anti-HPA-1a. Transfusion. 2005; 45(12):1945-1956.
11. Curtis B R, McFarland J G. Human platelet antigens—2013. Vox Sang. 2014; 106(2):93-102.
12. Davoren A, Curtis B R, Aster R H, McFarland J G. Human platelet antigen-specific alloantibodies implicated in 1162 cases of neonatal alloimmune thrombocytopenia. Transfusion. 2004; 44(8):1220-1225.
13. Newman P J, Derbes R S, Aster R H. The human platelet alloantigens, PlA1 and PlA2, are associated with a leucine33/proline33 amino acid polymorphism in membrane glycoprotein IIIa, and are distinguishable by DNA typing. J Clin Invest. 1989; 83:1778-1781.
14. Goldberger A, Kolodziej M, Poncz M, Bennett J S, Newman P J. Effect of single amino acid substitutions on the formation of the PlA and Bak alloantigenic epitopes. Blood. 1991; 78:681-687.
15. Valentin N, Vergracht A, Bignon J D, et al. HLA-DRw52a is involved in alloimmunization against PlA1 antigen. Hum Immunol. 1990; 27:73-79.
16. Maslanka K, Yassai M, Gorski J. Molecular identification of T cells that respond in a primary bulk culture to a peptide derived from a platelet glycoprotein implicated in neonatal alloimmune thrombocytopenia. J Clin Invest. 1996; 98:1802-1808.
17. Ahlen M T, Husebekk A, Killie M K, Skogen B, Stuge T B. T-cell responses associated with neonatal alloimmune thrombocytopenia: isolation of HPA-1a-specific, HLA-DRB3*0101-restricted CD4+ T cells. Blood. 2009; 113(16):3838-3844.
18. Xiao T, Takagi J, Coller B S, Wang J H, Springer T A. Structural basis for allostery in integrins and binding to fibrinogen-mimetic therapeutics. Nature. 2004; 432 (7013):59-67.
19. Valentin N, Visentin G P, Newman P J. Involvement of the cysteine-rich domain of glycoprotein IIIa in the expression of the human platelet alloantigen, PlA1: evidence for heterogeneity in the humoral response. Blood. 1995; 85(11):3028-3033.
20. Weiss E J, Goldschmidt-Clermont P J, Grigoryev D, Jin Y, Kickler T S, Bray P F. A monoclonal antibody (SZ21) specific for platelet GPIIIa distinguishes P1A1 from P1A2. Tissue Antigens. 1995; 46(5):374-381.
21. Eksteen M, Tiller H, Averina M, et al. Characterization of a human platelet antigen-1a-specific monoclonal antibody derived from a B cell from a woman alloimmunized in pregnancy. J Immunol. 2015; 194(12):5751-5760.
22. Griffin H M, Ouwehand W H. A human monoclonal antibody specific for the leucine-33 (P1A1, HPA-1a) form of platelet glycoprotein IIIa from a V gene phage display library. Blood. 1995; 86(12):4430-4436.
23. Zhu G, Zhang Q, Reddy E C, et al. The integrin PSI domain has an endogenous thiol isomerase function and is a novel target for antiplatelet therapy. Blood. 2017; 129 (13):1840-1854.

24. Pidard D, Montgomery R R, Bennett J S, Kunicki T J. Interaction of AP-2, a monoclonal antibody specific for the human platelet glycoprotein IIb-IIIa complex, with intact platelets. J Biol Chem. 1983; 258:12582-12586.
25. Sivasubramanian A, Sircar A, Chaudhury S, Gray J J. Toward high-resolution homology modeling of antibody Fv regions and application to antibody-antigen docking. Proteins. 2009; 74(2):497-514.
26. Marze N A, Lyskov S, Gray J J. Improved prediction of antibody VL-VH orientation. Protein Eng Des Sel. 2016; 29(10):409-418.
27. Weitzner B D, Gray J J. Accurate Structure Prediction of CDR H3 Loops Enabled by a Novel Structure-Based C-Terminal Constraint. J Immunol. 2017; 198(1):505-515.
28. Weitzner B D, Jeliazkov J R, Lyskov S, et al. Modeling and docking of antibody structures with Rosetta. Nat Protoc. 2017; 12(2):401-416.
29. Lyskov S, Chou F C, Conchuir S O, et al. Serverification of molecular modeling applications: the Rosetta Online Server that Includes Everyone (ROSIE). PLoS One. 2013; 8(5):e63906.
30. Zhu J, Luo B H, Xiao T, Zhang C, Nishida N, Springer T A. Structure of a complete integrin ectodomain in a physiologic resting state and activation and deactivation by applied forces. Mol Cell. 2008; 32(6):849-861.
31. Comeau S R, Gatchell D W, Vajda S, Camacho C J. ClusPro: an automated docking and discrimination method for the prediction of protein complexes. Bioinformatics. 2004; 20(1):45-50.
32. Comeau S R, Gatchell D W, Vajda S, Camacho C J. ClusPro: a fully automated algorithm for protein-protein docking. Nucleic Acids Res. 2004; 32(Web Server issue): W96-99.
33. Kozakov D, Brenke R, Comeau S R, Vajda S. PIPER: an FFT-based protein docking program with pairwise potentials. Proteins. 2006; 65(2):392-406.
34. Kozakov D, Beglov D, Bohnuud T, et al. How good is automated protein docking? Proteins. 2013; 81(12):2159-2166.
35. Kozakov D, Hall D R, Xia B, et al. The ClusPro web server for protein-protein docking. Nat Protoc. 2017; 12(2):255-278.
36. Brenke R, Hall D R, Chuang G Y, et al. Application of asymmetric statistical potentials to antibody-protein docking. Bioinformatics. 2012; 28(20):2608-2614.
37. Barron-Casella E A, Nebbia G, Rogers O C, King K E, Kickler T S, Casella J F. Construction of a human platelet alloantigen-1a epitope(s) within murine glycoprotein IIIa: identification of residues critical to the conformation of the antibody binding site(s). Blood. 1999; 93(9):2959-2967.
38. Honda S, Honda Y, Bauer B, Ruan C, Kunicki T J. The impact of three-dimensional structure on the expression of PIA alloantigens on human integrin beta 3. Blood. 1995; 86(1):234-242.
39. Newman P J, Martin L S, Knipp M A, Kahn R A. Studies on the nature of the human platelet alloantigen, PlA1: localization to a 17,000-dalton polypeptide. Mol Immunol. 1985; 22:719-729.
40. Kornecki E, Chung S Y, Holt J C, Cierniewski C S, Tuszynski G P, Niewiarowski S. Identification of PlA1 alloantigen domain on a 66 kDa protein derived from glycoprotein IIIa of human platelets. Biochim Biophys Acta. 1985; 818(3):285-290.
41. Beer J, Coller B S. Evidence that platelet glycoprotein IIIa has a large disulfide-bonded loop that is susceptible to proteolytic cleavage. J Biol Chem. 1989; 264:17564-17573.
42. Flug F, Espinola R, Liu L X, et al. A 13-mer peptide straddling the leucine33/proline33 polymorphism in glycoprotein IIIa does not define the PlA1 epitope. Blood. 1991; 77:1964-1969.
43. Bowditch R D, Tani P H, Halloran C E, Frelinger A L, III, McMillan R, Ginsberg M H. Localization of a PlA1 epitope to the amino terminal 66 residues of platelet glycoprotein IIa. Blood. 1992; 79:559-562.
44. Stafford P, Ghevaert C, Campbell K, et al. Immunologic and structural analysis of eight novel domain-deletion beta3 integrin peptides designed for detection of HPA-1 antibodies. J Thromb Haemost. 2008; 6(2):366-375.
45. Ghevaert C, Campbell K, Stafford P, et al. HPA-1a antibody potency and bioactivity do not predict severity of fetomaternal alloimmune thrombocytopenia. Transfusion. 2007; 47(7):1296-1305.
46. Killie M K, Husebekk A, Kaplan C, Taaning E, Skogen B. Maternal human platelet antigen-1a antibody level correlates with the platelet count in the newborns: a retrospective study. Transfusion. 2007; 47(1):55-58.
47. Santoso S, Wihadmadyatami H, Bakchoul T, et al. Antiendothelial alphavbeta3 Antibodies Are a Major Cause of Intracranial Bleeding in Fetal/Neonatal Alloimmune Thrombocytopenia. Arterioscler Thromb Vasc Biol. 2016; 36(8):1517-1524.
48. Zhou D, Thinn A M M, Zhao Y, Wang Z, Zhu J. Structure of an extended beta3 integrin. Blood. 2018; 132(9):962-972.
49. Duquesnoy R J. The eplet load concept in clinical transplantation. Pediatr Transplant. 2016; 20(7):884-885.
50. Duquesnoy R J. Structural epitope matching for HLA-alloimmunized thrombocytopenic patients: a new strategy to provide more effective platelet transfusion support? Transfusion. 2008; 48(2):221-227.
51. Brooks E G, MacPherson B R, Fung M K. Validation of HLAMatchmaker algorithm in identifying acceptable HLA mismatches for thrombocytopenic patients refractory to platelet transfusions. Transfusion. 2008; 48(10): 2159-2166.
52. Watkins N A, Schaffner-Reckinger E, Allen D L, et al. HPA-1a phenotype-genotype discrepancy reveals a naturally occurring Arg93Gln substitution in the platelet beta 3 integrin that disrupts the HPA-1a epitope. Blood. 2002; 99(5):1833-1839.
53. Thinn A M M, Wang Z, Zhou D, Zhao Y, Curtis B R, Zhu J. Autonomous conformational regulation of beta3 integrin and the conformation-dependent property of HPA-1a alloantibodies. Proc Natl Acad Sci USA. 2018.
54. Hod E1, Schwartz J., Platelet transfusion refractoriness. Br J Haematol. 2008 July; 142(3):348-60. Epub 2008 May 28.

We claim:

1. A transgenic mouse whose genome comprises a nucleic acid encoding a variant platelet membrane glycoprotein IIIa (GPIIIa) comprising SEQ ID NO: 25, wherein the variant GPIIIa comprises mutations T30A, S32P, Q33L, N39D, and M470Q in SEQ ID NO: 25, wherein the variant GPIIIa is expressed on platelets of the transgenic mouse, and wherein the variant GPIIIa can bind to an anti-HPA-1a antibody.

2. The transgenic mouse of claim 1, wherein the anti-HPA-1a antibody is monoclonal antibody 26.4.

* * * * *

UNITED STATES PATENT AND TRADEMARK OFFICE
CERTIFICATE OF CORRECTION

| | |
|---|---|
| PATENT NO. | : 11,266,129 B2 |
| APPLICATION NO. | : 16/674804 |
| DATED | : March 8, 2022 |
| INVENTOR(S) | : Peter J. Newman et al. |

It is certified that error appears in the above-identified patent and that said Letters Patent is hereby corrected as shown below:

In the Specification

Column 3, Line 4, "IIIc" should be --IIIa--.

Column 3, Line 27, "IIIc" should be --IIIa--.

Column 4, Line 56, "IIIc" should be --IIIa--.

Column 4, Line 65, "IIIc" should be --IIIa--.

Column 11, Line 51, "charactetistics" should be --characteristics--.

Column 16, Line 65, "IIIc" should be --IIIa--.

Column 18, Line 41, "er at." should be --et al.--.

Column 19, Line 34, "(MA)" should be --(RIA)--.

Signed and Sealed this
Nineteenth Day of July, 2022

Katherine Kelly Vidal
*Director of the United States Patent and Trademark Office*